US012752025B2

(12) United States Patent
Liu et al.

(10) Patent No.: US 12,752,025 B2
(45) Date of Patent: Oct. 6, 2026

(54) FIBROBLAST ACTIVATION PROTEIN INHIBITOR

(71) Applicant: BOOMRAY PHARMACEUTICALS CO., LTD., Suzhou City (CN)

(72) Inventors: Zhibo Liu, Jiangsu (CN); Mengxin Xu, Jiangsu (CN); Junyi Chen, Jiangsu (CN)

(73) Assignee: BOOMRAY PHARMACEUTICALS CO., LTD., Beijing (CN)

( * ) Notice: Subject to any disclaimer, the term of this patent is extended or adjusted under 35 U.S.C. 154(b) by 518 days.

(21) Appl. No.: 18/258,379

(22) PCT Filed: Dec. 20, 2021

(86) PCT No.: PCT/CN2021/139591

§ 371 (c)(1),
(2) Date: Jun. 20, 2023

(87) PCT Pub. No.: WO2022/135326

PCT Pub. Date: Jun. 30, 2022

(65) Prior Publication Data

US 2024/0042066 A1 Feb. 8, 2024

(30) Foreign Application Priority Data

Dec. 21, 2020 (CN) ........................ 202011519183.X

(51) Int. Cl.
*A61K 51/04* (2006.01)
*A61P 35/00* (2006.01)

(52) U.S. Cl.
CPC .......... *A61K 51/0497* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 8,344,177 B2 * | 1/2013 | Neri | ........................ | A61P 35/00 562/444 |
| 2021/0038749 A1 * | 2/2021 | Haberkorn | ........... | A61K 49/106 |

FOREIGN PATENT DOCUMENTS

| | | | |
|---|---|---|---|
| CN | 111699181 | 9/2020 | |
| CN | 112105354 | 12/2020 | |
| WO | 2019/190266 A1 | 3/2019 | |
| WO | 2019/154886 A1 | 8/2019 | |
| WO | 2020205948 | 10/2020 | |
| WO | WO-2020205948 A1 * | 10/2020 | ......... A61K 51/0497 |

OTHER PUBLICATIONS

Lindner, et al., (2020) "Design and development of 99mTc-Labeled FAPI tracers for SPECT imaging and 188Re Therapy," J Nucl Med, 61:1507-1513.

English Translation of International Search Report (ISR) for PCT/CN2021/139591 dated Mar. 7, 2022, pp. 1-2.

* cited by examiner

*Primary Examiner* — Celeste A Roney
(74) *Attorney, Agent, or Firm* — McDonnell Boehnen Hulbert & Berghoff, LLP

(57) ABSTRACT

Provided are a compound as represented by general formula (I) or a pharmaceutically acceptable salt, a stereoisomer or a solvate thereof, wherein C is a chelator unit; AB is an albumin binding unit; and FAPI is a fibroblast activation protein inhibitor unit. Also provided are a chelate of the above-mentioned compound and a radioactive nuclide, a pharmaceutical composition and the use thereof as a fibroblast activation protein inhibitor for the diagnosis and treatment of diseases.

C-AB-FAPI (1)

13 Claims, 5 Drawing Sheets

FIG. 4
Inhibition group
Non-inhibition group

FIBROBLAST ACTIVATION PROTEIN INHIBITOR

CROSS-REFERENCE TO RELATED APPLICATIONS

The present application is a U.S. national phase of International Application No. PCT/CN2021/139591, filed on Dec. 20, 2021, which claims priority to Chinese Patent Application No. 202011519183.X filed on Dec. 21, 2020, which is incorporated herein by reference in its entirety.

TECHNICAL FIELD

The present disclosure relates to the field of medical treatment and diagnosis, in particular to compounds, chelates and compositions for inhibiting fibroblast activation proteins, and use of the same.

BACKGROUND

As the second leading cause of death, tumor is a threat to people's health. Tumors can be considered as both a collection of malignant cells and a collection of stromal cells, including vascular cells, inflammatory cells and fibroblasts. In tumors with fibroproliferative responses such as breast cancer, colon cancer and pancreatic cancer, the stroma in tumors may account for 90% or more. A subpopulation of fibroblasts in tumor stromata, referred to as cancer-associated fibroblasts (CAFs), are involved in tumor growth, migration and progression, and even cause resistance and immunosuppression to chemotherapy.

Tumor microenvironment (TME) around tumors plays an important role in the occurrence and development of tumors, and TME is centered around activated fibroblasts (CAFs). Fibroblast activation protein (FAP) is a type II transmembrane serine proteolytic enzyme belonging to the dipeptidyl peptidase (DPP) family. FAP is selectively expressed in CAFs of more than 90% of epithelial malignant tumors, but hardly expressed in normal tissues, and has special biological characteristics and gene stability. FAP is widely expressed in the microenvironment of various tumors, and therefore, can be targeted for different tumor entities, including pancreatic cancer, breast cancer and lung cancer, which account for a large portion of solid tumors. Therefore, FAP not only can be used as a biomarker for early diagnosis of tumors, but also has good biological characteristics for targeted therapy, which is expected to play an important role in clinical diagnosis and treatment of malignant tumors.

Currently, there is still no in-depth research on FAP inhibitors, and the first FAP activity inhibitor that entered clinical trials is Talabostat, but Talabostat has shown insufficient clinical activity in various cancers, and therefore, no further development has been made. Later, some researchers conducted tumor treatment research by using $^{131}$I-labeled anti-FAP antibody sibrotuzumab, but sibrotuzumab has defects such as a low clearance rate and a lack of clinical activity.

In the past two years, Haberkorn Uwe team at Heidelberg University in Germany developed a series of quinoline-based small molecule radiopharmaceuticals targeting FAP for diagnosis and treatment (see WO2019154886A1). The produced inhibitor can rapidly and nearly completely bind to human and mouse FAP. Importantly, the produced inhibitor does not cross-react with DPP family member DPP4, thereby laying the foundation for further development. By connecting the FAP inhibitor (FAPI) with a chelator DOTA, a radioactive nuclide tracer with good pharmacokinetic properties is formed. The most concerned tracer is FAPI-04, which has higher affinity for FAP, and is quickly cleared from the blood and by the kidney. With these properties, $^{68}$Ga-FAPI-04 PET/CT tumor imaging has high contrast and high sensitivity. However, due to the rapid elution of FAPI-04 in vivo, its application in tumor radionuclide therapy is limited. Therefore, it is particularly desirable to maintain its excellent targeting property and solve the problem of short circulation time of FAP inhibitor small molecules.

SUMMARY

An aspect of the present disclosure provides a compound of general formula (I), or a pharmaceutically acceptable salt, an isomer or a solvate thereof,

C-AB-FAPI (I)

where C is a chelator unit; AB is an albumin binding unit; and FAPI is a fibroblast activation protein inhibitor unit.

In some embodiments, the unit C in general formula (I) is selected from:

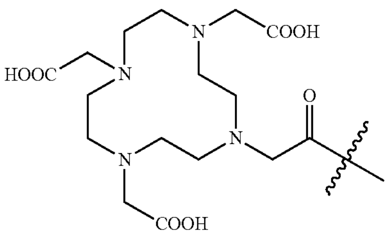

,

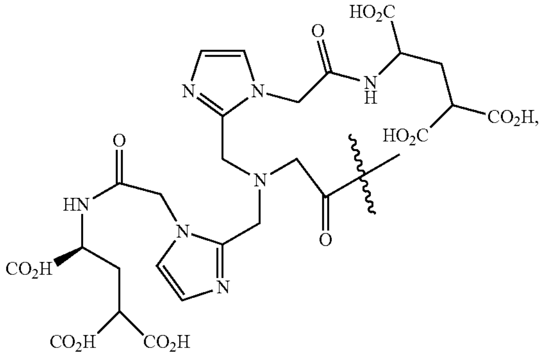

-continued
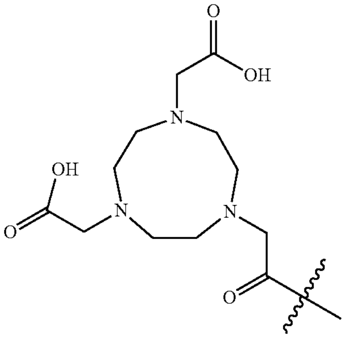
,
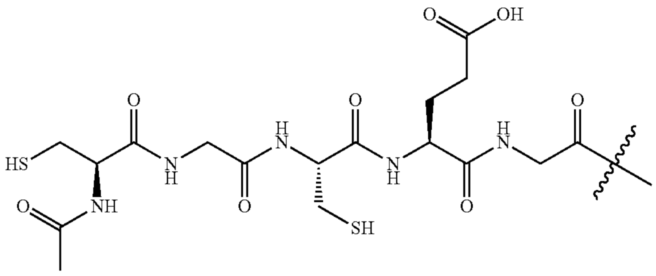
,
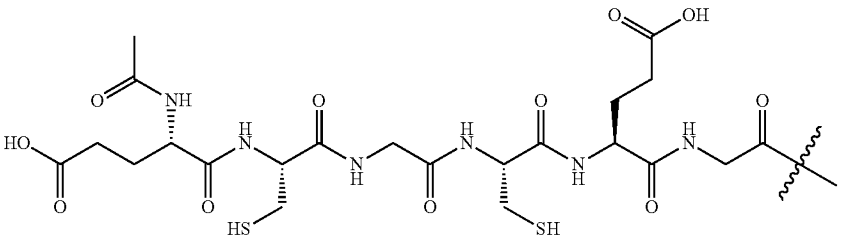
,
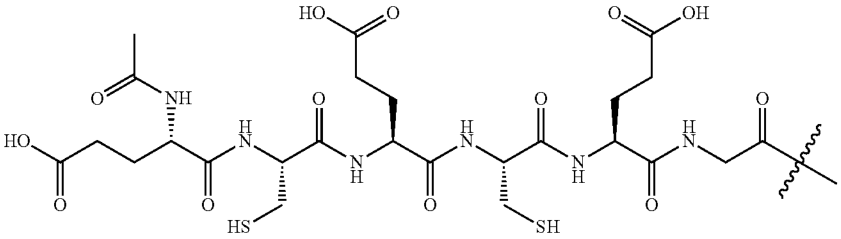
or
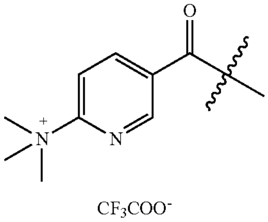
.
In some embodiments, the unit FAPI in general formula (I) is selected from:
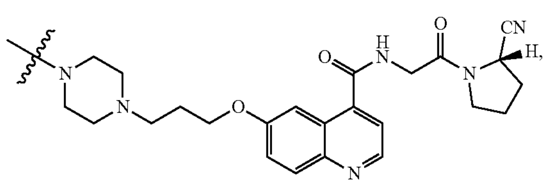
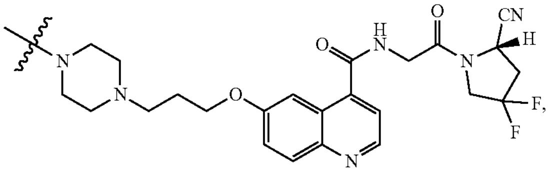
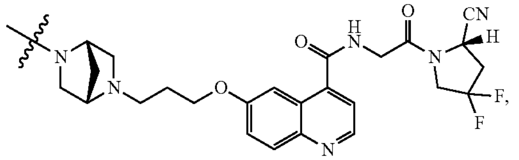
or
-continued
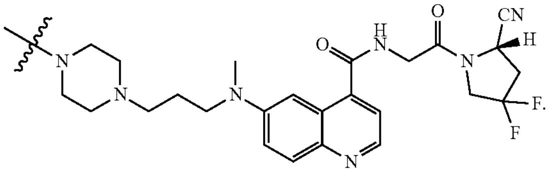
In some embodiments, the unit AB in general formula (I) comprises a 4-iodo-phenyl group
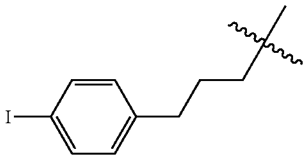
as an end group.
In some embodiments, the unit AB in general formula (I) is selected from

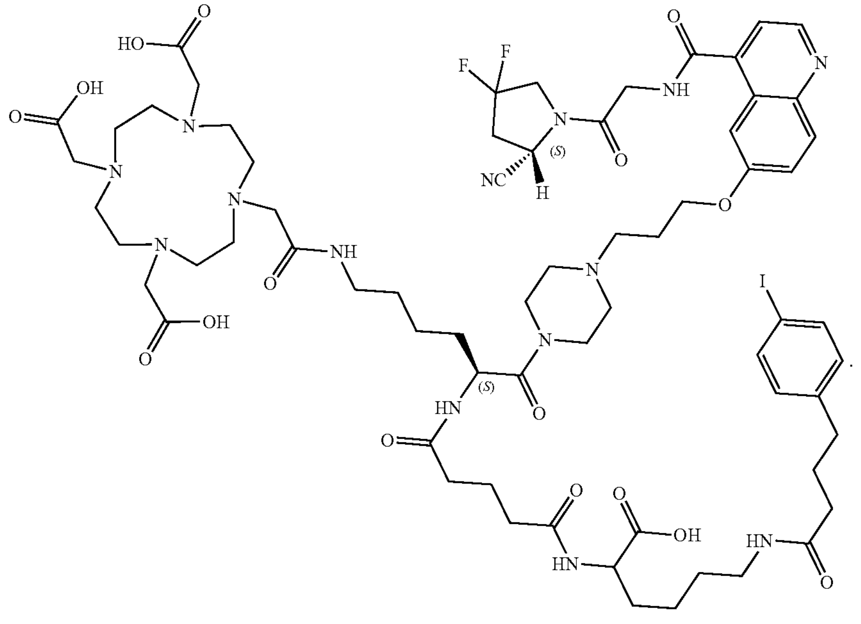

In some embodiments, the unit AB is connected to the unit FAPI by forming an amide bond with

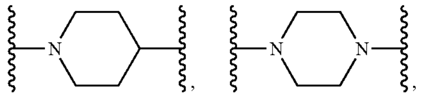

-continued

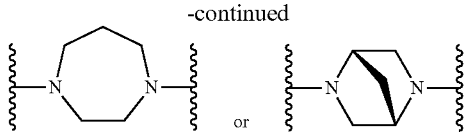

at an end of the unit FAPI, and the unit AB is connected to the unit C by forming an amide bond with a carbonyl group at an end of the unit C.

In some specific embodiments, the compound of general formula (I) is

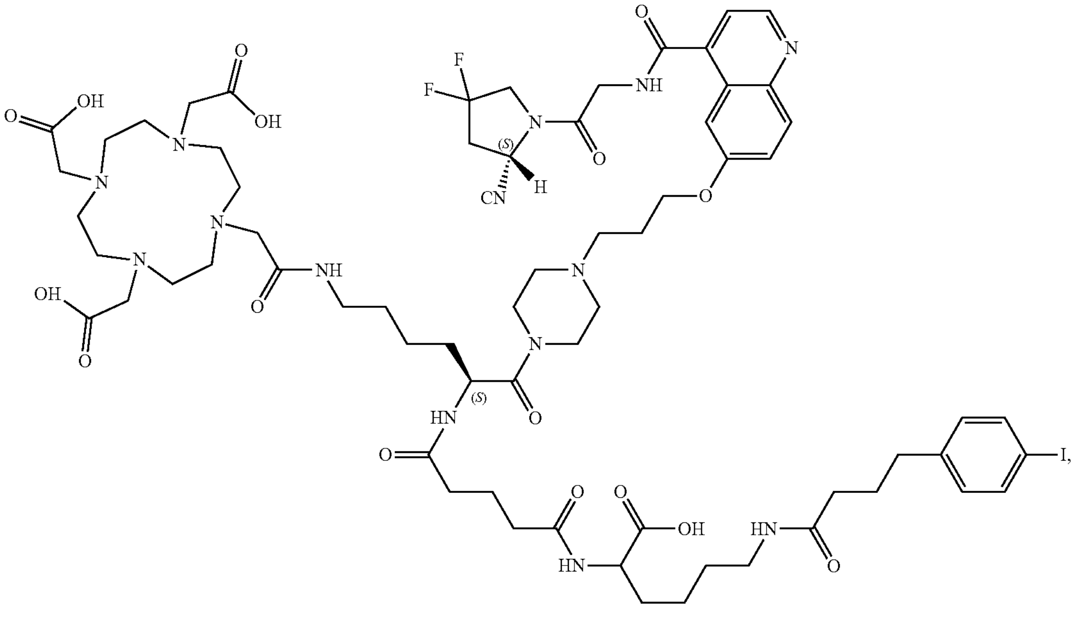

or a pharmaceutically acceptable salt, an isomer or a solvate thereof.

Another aspect of the present disclosure provides a chelate comprising the compound of formula (I) and a radioactive nuclide.

In some embodiments, the radioactive nuclide is selected from one or more of $^{18}F$, $^{51}Cr$, $^{67}Ga$, $^{68}Ga$, $^{111}In$, $^{99}mTc$, $^{186}Re$, $^{188}Re$, $^{139}La$, $^{140}La$, $^{175}Yb$, $^{15}3Sm$, $^{166}Ho$, 86Y, $^{88}Y$, $^{90}Y$, $^{149}Pm$, $^{165}Dy$, $^{169}Er$, $^{177}Lu$, $^{47}Sc$, $^{142}Pr$, $^{159}Gd$, $^{212}Bi$, $^{213}Bi$, $^{72}As$, $^{72}Se$, $^{97}Ru$, $^{109}Pd$, $^{105}Rh$, $^{101m}Rh$, $^{119}Sb$, $^{128}Ba$, $^{123}I$, $^{124}I$, $^{131}I$, $^{197}Hg$, $^{211}At$, $^{151}Eu$, $^{153}Eu$, $^{169}Eu$, $^{201}Tl$, $^{203}Pb$, $^{212}Pb$, $^{64}Cu$, $^{67}Cu$, $^{188}Re$, $^{186}Re$, $^{198}Au$, $^{225}Ac$, $^{227}Th$ and $^{199}Ag$.

In some specific embodiments, the radioactive nuclide is $^{68}Ga$, $^{86}Y$ or $^{177}Lu$.

A still another aspect of the present disclosure provides a pharmaceutical composition comprising or consisting of: at least one compound of formula (I) and optionally, a pharmaceutically acceptable excipient.

A yet another aspect of the present disclosure further provides use of the above chelate or the pharmaceutical composition in preparation of a reagent or a kit for diagnosis or treatment of a disease characterized by overexpression of fibroblast activation protein (FAP) in a subject.

A still yet another aspect of the present disclosure further provides a method of diagnosing or treating a disease characterized by overexpression of fibroblast activation protein (FAP) in a subject, including administering an effective dose of the above chelate or pharmaceutical composition to a subject in need of treatment.

A further aspect of the present disclosure further provides the above chelate or pharmaceutical composition for use in diagnosis or treatment of a disease characterized by overexpression of fibroblast activation protein (FAP) in a subject.

In some embodiments, the disease characterized by the overexpression of the fibroblast activation protein (FAP) is selected from cancer, chronic inflammation, atherosclerosis, fibrosis, tissue remodeling and keloidosis, and preferably, the cancer is selected from one or more of breast cancer, pancreatic cancer, small intestine cancer, colon cancer, rectal cancer, lung cancer, head and neck cancer, ovarian cancer, hepatocellular carcinoma, esophageal cancer, hypopharyngeal cancer, nasopharyngeal cancer, laryngeal cancer, myeloma cells, bladder cancer, cholangiocarcinoma, clear cell renal carcinoma, neuroendocrine tumor, carcinogenic osteomalacia, sarcoma, CUP (carcinoma of unknown primary), thymic carcinoma, glioma, neuroglioma, astrocytoma, cervical cancer and prostate cancer.

A still further aspect of the present disclosure further provides a kit comprising or consisting of the above chelate or pharmaceutical composition, and an instruction for diagnosing or treating a disease.

BRIEF DESCRIPTION OF THE DRAWINGS

In order to describe the technical solutions of the embodiments of the present disclosure more clearly, the following briefly describes the accompanying drawings of the embodiments. Apparently, the accompanying drawings in the following description merely relate to some embodiments of the present disclosure, but are not intended to limit the present invention.

DETAILED DESCRIPTION

Figure 1:
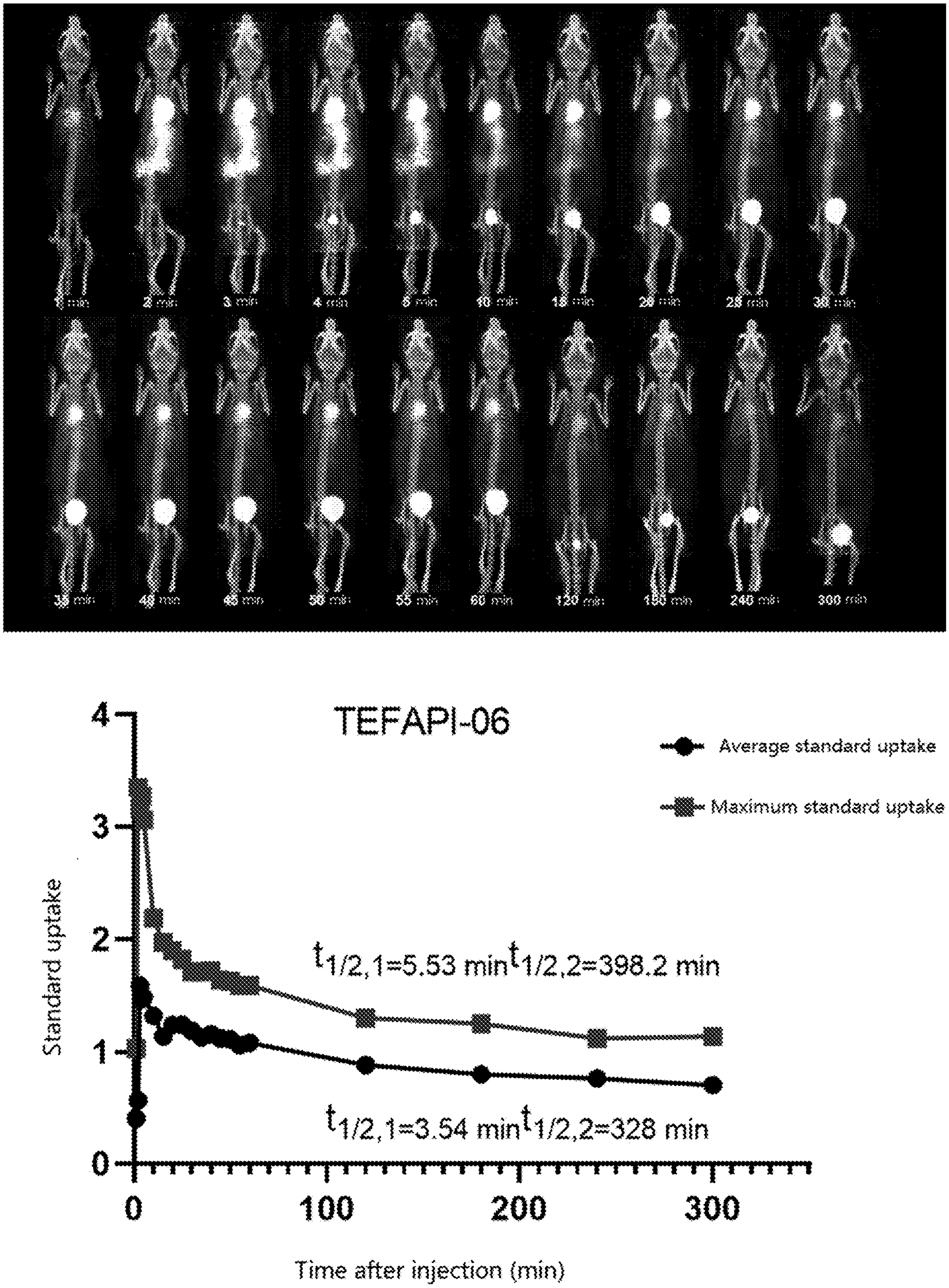
FIG. 1 shows results of measuring half-life in vivo by imaging healthy mice with $^{68}Ga$-TEFAPI-06.

In order to make the purpose, technical solutions, and advantages of the examples of the present disclosure clearer, the following describes the technical solutions in the examples of the present disclosure clearly and completely with reference to accompanying drawings of the examples of the present disclosure. Apparently, the described examples are merely some rather than all of the examples of the present disclosure. All other embodiments obtained by a person of ordinary skill in the art based on the described examples of the present disclosure without inventive efforts shall fall within the protection scope of the present invention.

The present invention may be implemented in another specific form without departing from a basic feature of the present invention. It should be understood that any and all embodiments of the present invention can be combined with technical features in any one or more other embodiments to obtain additional embodiments without conflicts. The present invention includes the additional embodiments obtained through such combination.

All publications and patents mentioned in the present disclosure are hereby incorporated by reference into the present disclosure in their entirety. If application or a term used in any publications and patents incorporated by reference conflicts with application or a term used in the present disclosure, the application and term in the present disclosure shall prevail.

Section headings used herein are only intended to organize an article and should not be construed as a limitation on the theme.

Unless otherwise defined, all technical and scientific terms used herein have general meanings in the art to which the claimed theme belongs. If one specific term has multiple definitions, the definition herein shall prevail.

Unless otherwise specified, when any type of range is disclosed or claimed, it is intended that each possible value that could be reasonably encompassed in the range is individually disclosed or claimed, including any sub-range encompassed therein. For example, the number of substituents ranging from 1 to 5 indicates an integer within the range, and it should be understood that the range of 1 to 5 includes 1, 2, 3, 4 and 5, and also includes subranges of 1 to 4 and 1 to 3.

The description of the present disclosure should be construed as being in accordance with the rules and principles of chemical bonding. In some cases, a hydrogen atom may be removed in order to accommodate a substituent at a given position.

Similar words such as "comprise", "include" or "contain" used in the present disclosure mean that elements appearing before the word encompass elements listed after the word and their equivalents, and do not exclude unrecited elements. The term "include" or "comprise (contain)" used herein can be inclusive, semi-exclusive and exclusive. In other words, the term also includes "consisting essentially of" or "consisting of".

The term "pharmaceutically acceptable" in the present application means that a compound or composition is chemically and/or toxicologically compatible with other ingredients constituting a preparation and/or with the human or mammal administered with the compound or composition for prevention or treatment of a disease or a condition.

The term “subject” or “patient” in the present application includes humans and mammals.

In the context of the present application, unless specifically stated to the contrary, the term “treatment” may also include prevention.

The term “solvate” in the present application refers to a composite formed by combining a compound of formula (I) or a pharmaceutically acceptable salt thereof with a solvent. It should be understood that, although any solvate of the compound of formula (I) used in the diagnosis or treatment of the disease or condition in the present application may provide different features (including pharmacokinetic properties), once the solvate is absorbed into the subject, the compound of formula (I) is obtained, and therefore, the use of the compound of formula (I) encompasses the use of any solvate of the compound of formula (I).

The term “hydrate” refers to a case where the solvent in the above term “solvate” is water.

It should be further understood that the compound of formula (I) or the pharmaceutically acceptable salt thereof may be separated in the form of solvates, and therefore, any such solvates are included in the scope of the present invention. For example, the compound of formula (I) or the pharmaceutically acceptable salt thereof may exist in an unsolvated form and a solvated form formed with a pharmaceutically acceptable solvent (such as water, ethanol, etc.).

The term “pharmaceutically acceptable salt” refers to a relatively non-toxic addition salt of the compound of the present disclosure. For example, see S. M. Berge et al. “Pharmaceutical Salts”, J. Pharm. Sci. 1977, 66, 1-19.

Suitable pharmaceutically acceptable salts of the compound of the present disclosure may be, for example, acid addition salts of the compound of the present disclosure that are sufficiently basic to carry a nitrogen atom in a chain or ring, for example, an acid addition salt formed with an inorganic acid such as hydrochloric acid, hydrobromic acid, hydroiodic acid, sulfuric acid, phosphoric acid or nitric acid, or an acid addition salt formed with an organic acid such as formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid; 2-(4-hydroxybenzoyl)benzoic acid, camphoric acid, cinnamic acid, cyclopentanepropionic acid, 3-hydroxy-2-naphthoic acid, niacin, pamoic acid, pectinic acid, persulfuric acid, 3-phenylpropionic acid, picric acid, pivalic acid, 2-hydroxyethanesulfonic acid, itaconic acid, sulfamic acid, trifluoromethanesulfonic acid, laurylsulfuric acid, ethanesulfonic acid, benzenesulfonic acid, p-toluenesulfonic acid, methanesulfonic acid, 2-naphthalenesulfonic acid, naphthalene disulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid or thiocyanic acid.

In addition, another suitable pharmaceutically acceptable salt of a compound in the present invention that is sufficiently acidic is an alkali metal salt such as sodium salt or potassium salt, an alkaline earth metal salt such as calcium salt or magnesium salt, ammonium salt, or a salt formed with an organic base providing physiologically acceptable cations, for example, a salt formed with the following substance: N-methylglucamine, dimethylglucamine, ethylglucamine, lysine, dicyclohexylamine, 1,6-hexamethylenediamine, ethanolamine, glucosamine, sarcosine, serinol, tris(hydroxymethyl)aminomethane, aminopropylene glycol, or 1-amino-2,3,4-butanetriol. In addition, a basic nitrogen-containing group can be quaternized with the following reagents: lower alkyl halides such as chlorides, bromides and iodides of methyl, ethyl, propyl and butyl; dialkyl sulfates such as dimethyl sulfate, diethyl sulfate, dibutyl sulfate and diamyl sulfate; long-chain halides such as chlorides, bromides and iodides of decyl, lauryl, myristyl and stearyl; and aralkyl halides such as benzyl and phenethyl bromides.

Persons skilled in the art should also understand that an acid addition salt of the claimed compound may be prepared via reaction of the compound and a suitable inorganic or organic acid in any one of various known methods. Alternatively, the alkali metal and alkaline earth metal salts of the acidic compounds in the present disclosure are prepared via reaction of the acidic compound and an appropriate base in various known methods.

The present invention includes all possible salts of the compound of the present disclosures, which may be a single salt or any mixture of the salts in any ratio.

It should be understood that according to the context, the term “compound of the present disclosure” as used herein may include: the compound of formula (I), and a pharmaceutically acceptable salt and a solvate thereof, a solvate of the pharmaceutically acceptable salt of the compound, and a mixture thereof.

The compound of the present disclosure may contain one or more asymmetric centers, depending on the positions and properties of the desired various substituents. Asymmetric carbon atoms may exist in an (R) or (S) configuration, a racemic mixture is obtained in the case of one asymmetric center, and a diastereoisomer mixture is obtained in the case of multiple asymmetric centers. In some cases, asymmetry may also exist due to hindered rotation around a particular bond. For example, a central bond is connected to two substituted aromatic rings of a particular compound.

Preferred compounds are those that can produce more desirable biological activities. Isolated, purified or partially purified isomers and stereoisomers, or racemic or diastereoisomer mixtures of the compounds of the present disclosure all fall within the scope of the present invention. Purification and isolation of such substances can be achieved via standard techniques known in the art.

The “chelator unit” mentioned in the present disclosure with respect to the compound of general formula (I) refers to a molecular fragment derived from a chelator. For example, the chelator unit is a molecular fragment derived from 1,4,7,10-tetraazacyclododecane-N,N',N,N'-tetraacetic acid (DOTA), and may be introduced into the compound of general formula (I) by forming an amide

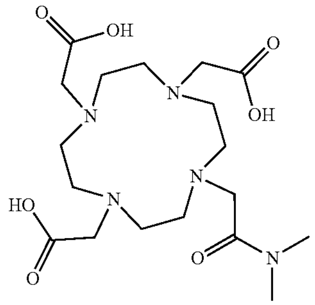

via a carboxyl group of DOTA.

The "fibroblast activation protein inhibitor unit" mentioned in the present disclosure with respect to the compound of general formula (I) refers to a molecular fragment derived from a fibroblast activation protein inhibitor. For example, when the inhibitor is a FAPI series compound disclosed in Table 1 and Table 3 in WO2019154886A1, the "fibroblast activation protein inhibitor unit" is a molecular fragment obtained by removing $R^8$ from the FAPI series compound.

The "albumin binding unit" mentioned in the present disclosure with respect to the compound of general formula (I) refers to a molecular fragment with high affinity for albumin, and the molecular fragment has a group connected with the chelator unit and the fibroblast activation protein inhibitor unit.

The "unit FAPI and unit C are formed together" mentioned in the present disclosure with respect to the compound of general formula (I) does not mean that the unit FAPI and the unit C are directly connected in the compound of general formula (I), but refers to a pseudo situation, that is, the unit FAPI and the unit C in the compound of the general formula (I) are taken out and connected (with the albumin binding unit therebetween removed).

It should be understood that a singular form (for example, "a") used in the present disclosure may include a plural referent, unless otherwise specified.

Unless otherwise specified, the present disclosure uses standard nomenclature and standard laboratory procedures and techniques of analytical chemistry, synthetic organic chemistry and coordination chemistry. Unless otherwise specified, the present disclosure uses conventional methods of mass spectrometry and elemental analysis, and for each step and condition, the conventional operation steps and conditions in the art may be referred to.

The reagents and raw materials used in the present disclosure are commercially available or can be prepared by conventional chemical synthesis methods.

When used to describe a specific situation herein, the term "optionally" means that the situation may or may not occur. For example, the term "optionally substituted" means being unsubstituted or having at least one non-hydrogen substituent that does not damage the desired properties possessed by the unsubstituted analog. For example, for a pharmaceutical composition, the expression "and optionally a pharmaceutically acceptable excipient" used herein means that the pharmaceutically acceptable excipient may or may not exist in the pharmaceutical composition.

In the present disclosure, unless otherwise specified, the number of "substituents" can be one or more; and when there are multiple substituents, there can be 2, 3 or 4 substituents. In addition, when the number of "substituents" is more than one, the "substituents" may be the same or different.

In the present disclosure, the position of "substitution" can be arbitrary unless otherwise specified.

The term "$C_1$-$C_{10}$ alkyl group" used herein refers to a linear or branched alkane chain having 1 to 10 carbon atoms. For example, representative examples of $C_1$-$C_6$ alkyl group include, but are not limited to, methyl ($C_1$), ethyl ($C_2$), n-propyl ($C_3$), isopropyl ($C_3$), n-butyl ($C_4$), t-butyl ($C_4$), sec-butyl ($C_4$), isobutyl ($C_4$), n-pentyl ($C_5$), 3-pentyl ($C_5$), neopentyl ($C_5$), 3-methyl-2-butanyl ($C_5$), tert-pentyl ($C_5$) group and n-hexyl ($C_6$) group. The term "lower alkyl group" refers to a linear or branched alkyl group having 1 to 4 carbon atoms. The "substituted alkyl group" refers to an alkyl group substituted with one or more substituents, preferably 1 to 4 substituents, at any available connecting site.

The term "haloalkyl group" refers to an alkyl group having one or more halogen substituents, including, but not limited to, groups such as $—CH_2Br$, $—CH_2I$, $—CH_2Cl$, $—CH_2F$, $—CHF_2$ and $—CF_3$.

The term "alkylene group" used herein refers to a divalent hydrocarbyl group that is similar to the above described "alkyl group" but has two connecting sites. For example, methylene is $—CH_2—$ group and ethylene is $—CH_2—CH_2—$ group.

The terms "alkoxy group" and "alkylthio group" used herein refer to the above alkyl groups connected via an oxygen bond (—O—) or a sulfur bond (—S—) respectively. The terms "substituted alkoxy group" and "substituted alkylthio group" refer to substituted alkyl groups connected via an oxygen bond or a sulfur bond, respectively. The "lower alkoxy group" is OR group in which R is a lower alkyl group (alkyl group containing 1 to 4 carbon atoms).

The term "halogen" used herein refers to fluorine, chlorine, iodine or bromine.

Albumin has been used increasingly widely as a drug carrier, and is often used to improve the hemodynamic properties of a drug, thereby increasing blood flow half-life. Albumin is the most abundant protein in human plasma, which undertakes various storage and transportation tasks in the body. Compared with normal tissues, tumor tissues have abundant blood vessels and larger vascular endothelial spaces. As a macromolecular substance, albumin can penetrate into tumor tissues but cannot enter normal tissues. In addition, substances with smaller molecular weight are cleared from tumor stroma faster, while macromolecules are trapped. Such effect is also known as enhanced permeability and retention effect (EPR) of macromolecule substances in tumor tissues. In addition, in tumor microenvironment, albumin binding receptors such as gp60 receptor and SPARC134 are highly expressed, which further retain albumin in the vicinity of the tumor. Therefore, using albumin as a carrier for anticancer drugs not only improves the half-life of these drugs, but also improves their delivery to and retention in the tumor. A drug-loaded albumin system mainly includes chemically coupled and physically bound drug-loaded albumin.

In the present disclosure, the albumin binding agent is connected with the chelator unit and the FAP inhibitor unit to form a small molecular compound (TEFAPI) capable of dual targeting FAP and albumin, with the purpose of prolonging the blood circulation half-life of the FAPI molecule and increasing tumor uptake.

The present disclosure provides a compound of general formula (I) or a pharmaceutically acceptable salt, an isomer or a solvate thereof;

C-AB-FAPI (I)

where C is a chelator unit; AB is an albumin binding unit; and FAPI is a fibroblast activation protein inhibitor unit.

In an embodiment, the unit C is derived from a chelator selected from the group consisting of 1,4,7,10-tetraazacyclododecane-N,N',N,N'-tetraacetic acid (DOTA), ethylenediaminetetraacetic acid (EDTA), 1,4,7-triazacyclononane-1,4,7-triacetic acid (NOTA), triethylenetetramine (TETA), iminodiacetic acid, diethylene triamine-N,N,N',N',N"-pentaacetic acid (DTPA), bis-(carboxymethylimidazole)glycine or 6-hydrazinopyridine-3-carboxylic acid (HYNIC).

For example, the unit C is

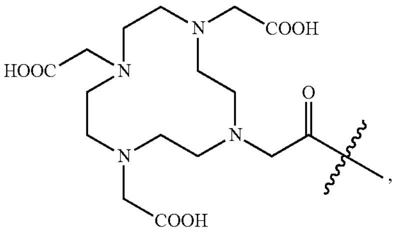 [SMILES: *C(=O)CN1CCN(CC(=O)O)CCN(CC(=O)O)CCN(CC(=O)O)CC1]

which is derived from 1,4,7,10-tetraazacyclododecane-N,N',N,N'-tetraacetic acid (DOTA), and may be introduced into the compound of general formula (I) by forming an amide

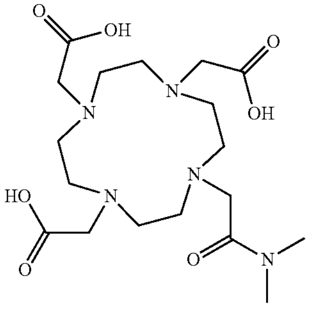

via a carboxyl group of DOTA.

For example, the unit C is

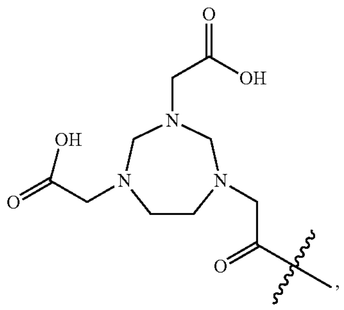 [SMILES: *C(=O)CN1CCN(CC(=O)O)CN(CC(=O)O)C1]

which is derived from 1,4,7-triazacyclononane-1,4,7-triacetic acid (NOTA), and may be introduced into the compound of general formula (I) by forming an amide

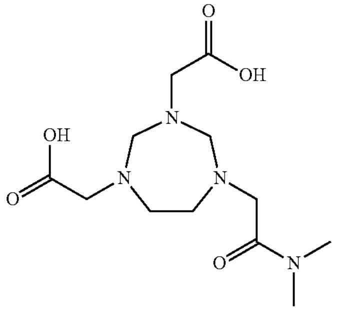

via a carboxyl group of NOTA.

In an embodiment, the unit C in the compound of general formula (I) is selected from:

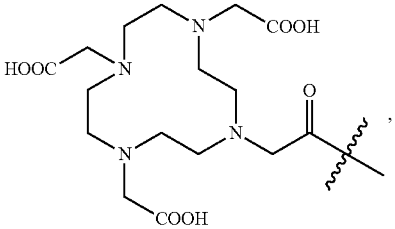
,
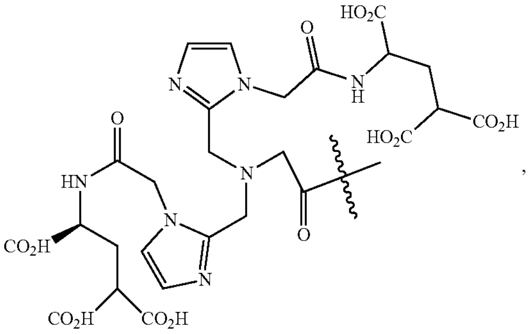
,
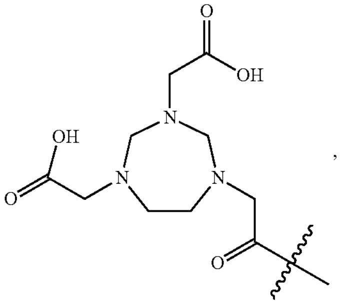
,
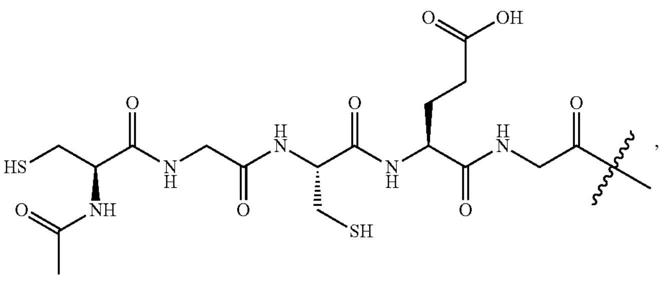
,

-continued

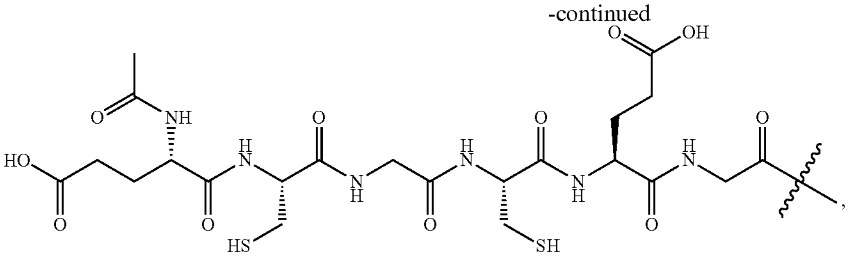

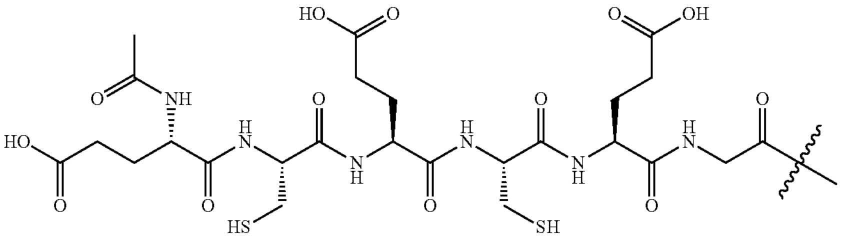

or

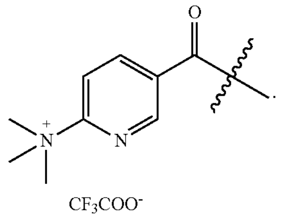

In an embodiment, the unit FAPI in the compound of general formula (I) is selected from:

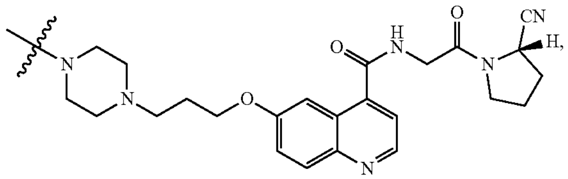

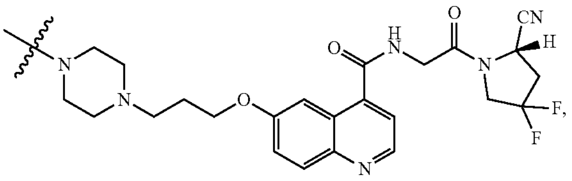

-continued

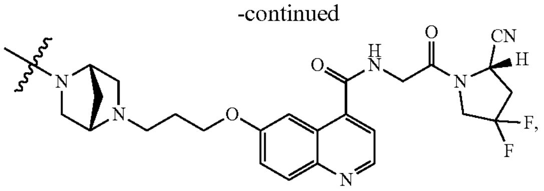

or

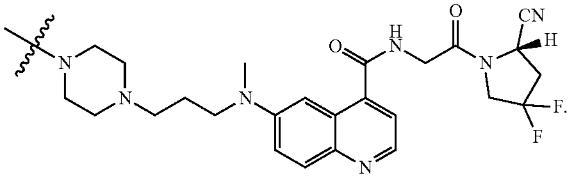

In an embodiment, the unit FAPI and the unit C in the compound of general formula (I) satisfy the following conditions:

If the unit FAPI and the unit C were connected (with the albumin binding unit therebetween removed), the new compound obtained through the connection would be selected from:

FAPI-02

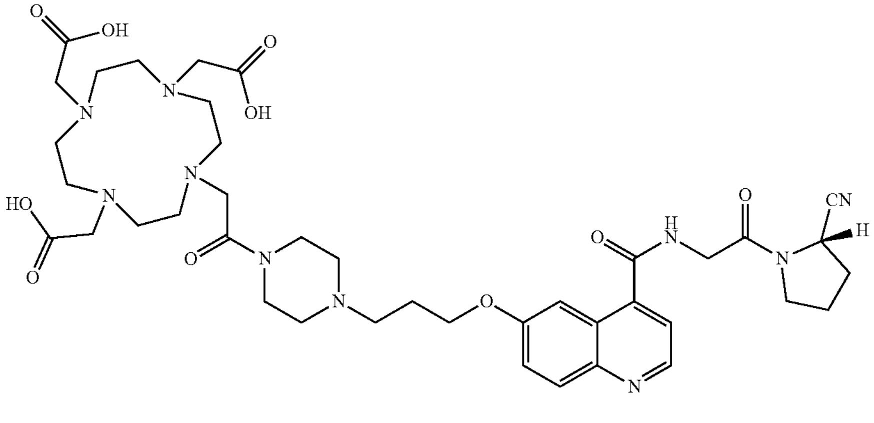

-continued
FAPI-04
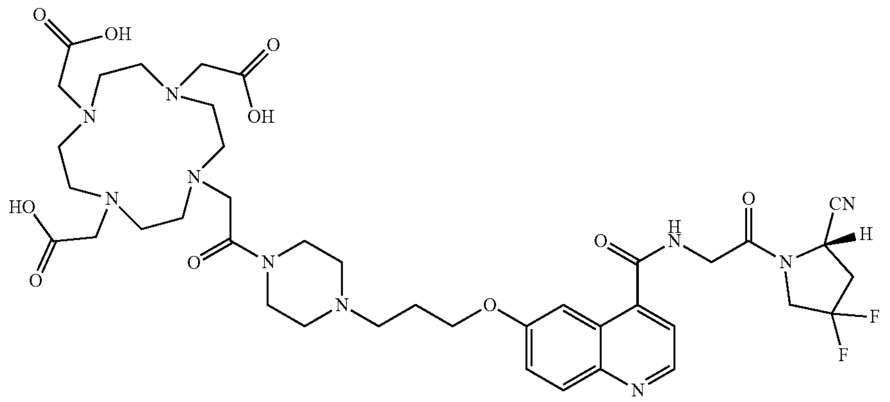
FAPI-21
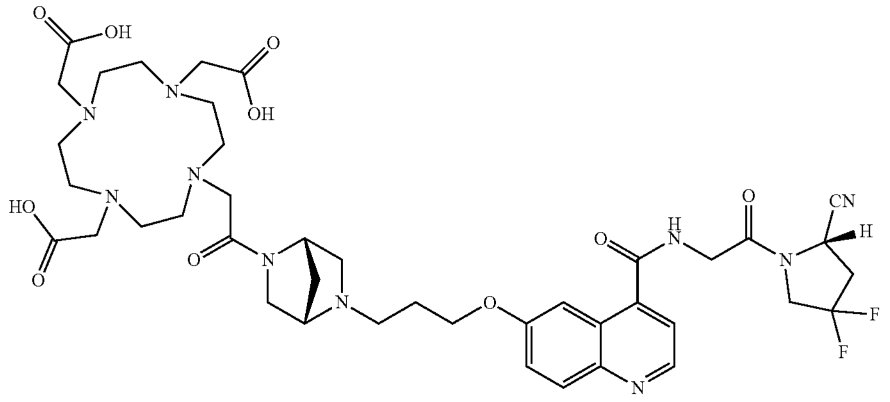
FAPI-34
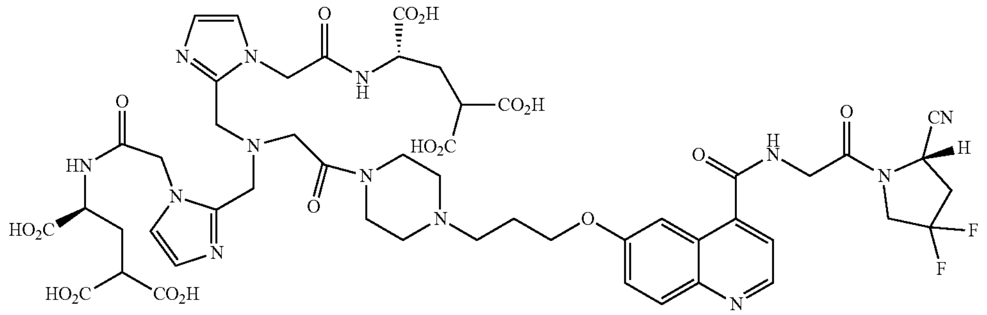
FAPI-42
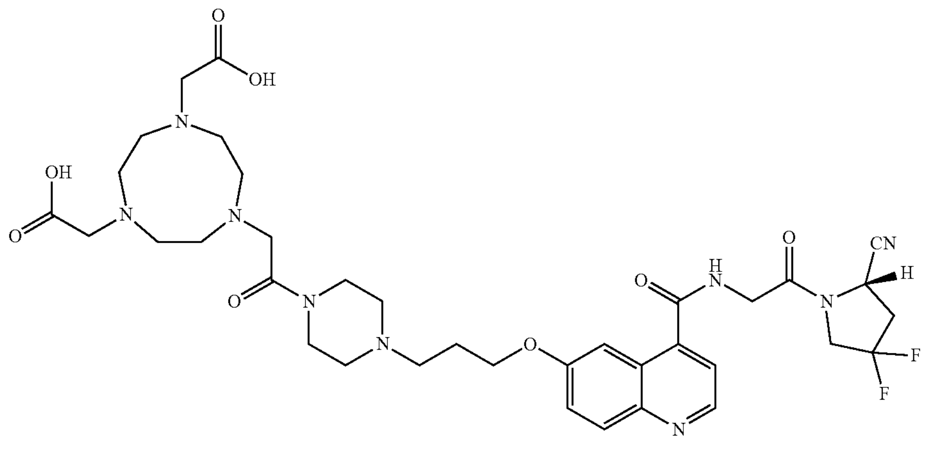

-continued
FAPI-46
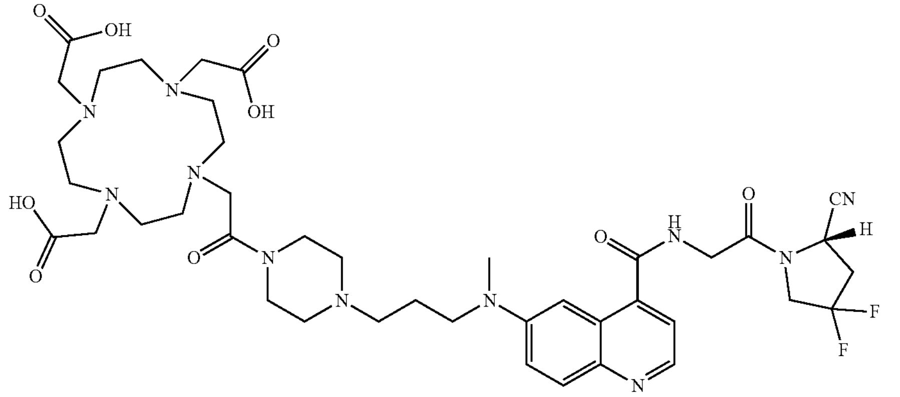
FAPI-52
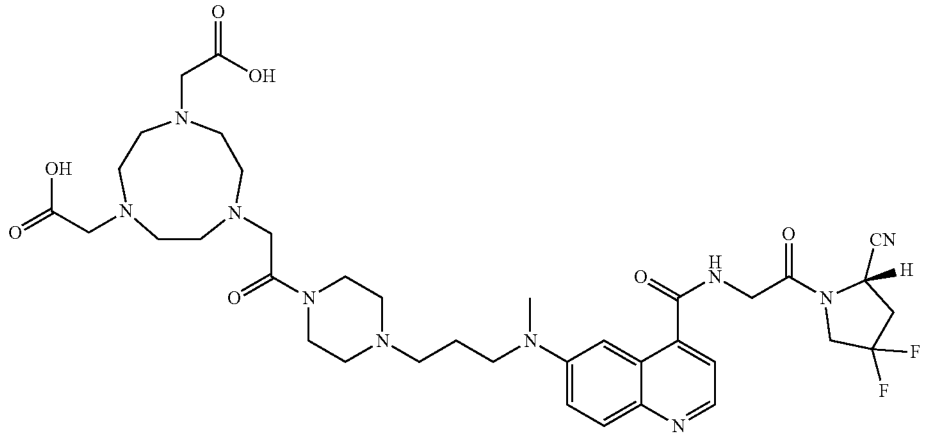
FAPI-69
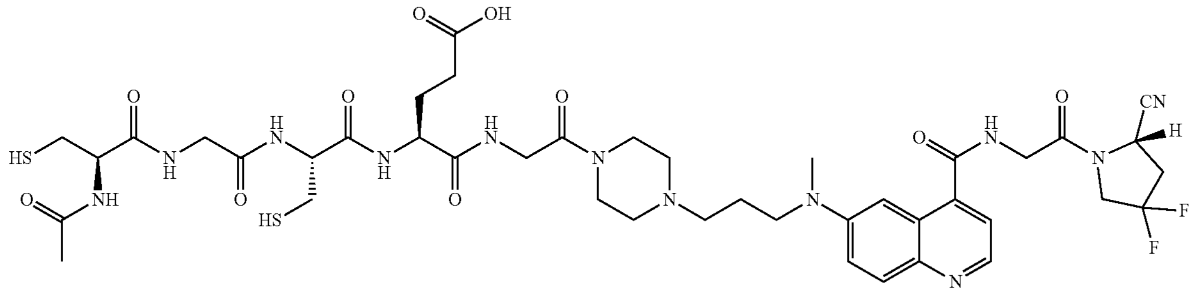
FAPI-70
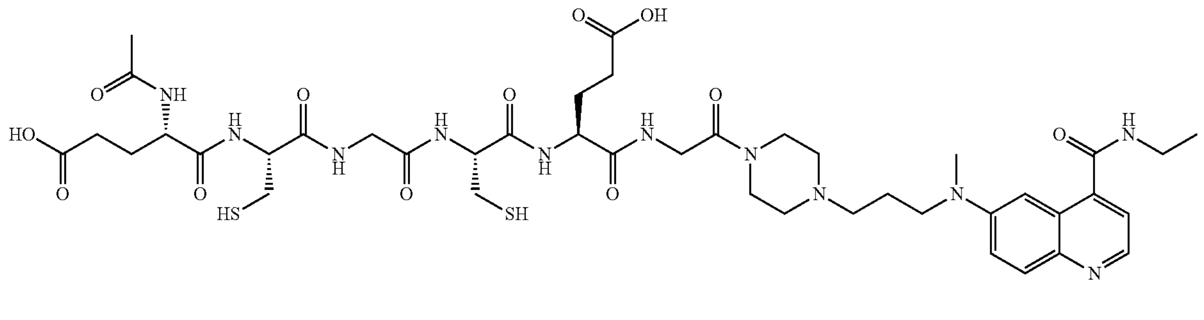

-continued

FAPI-71

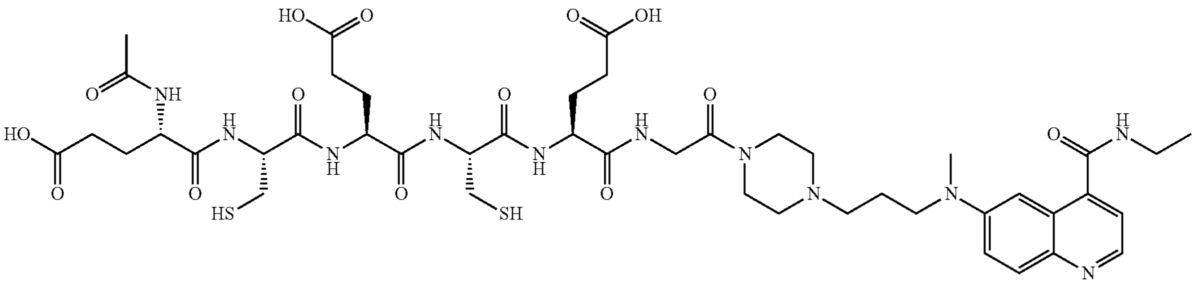

FAPI-72

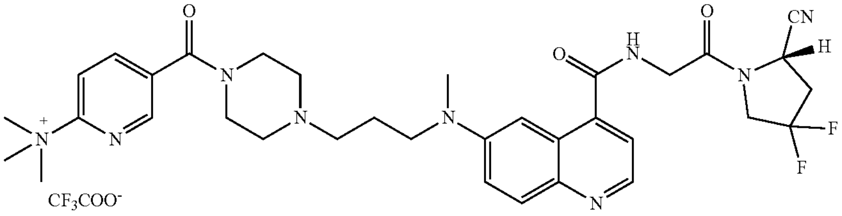

FAPI-73

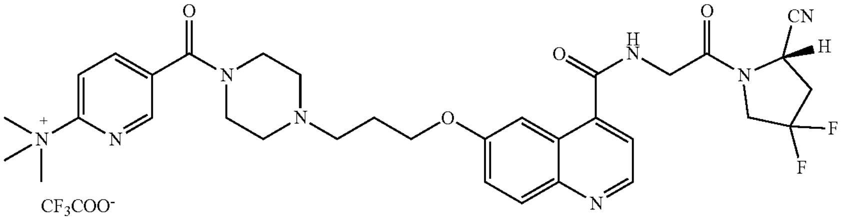

or

FAPI-74

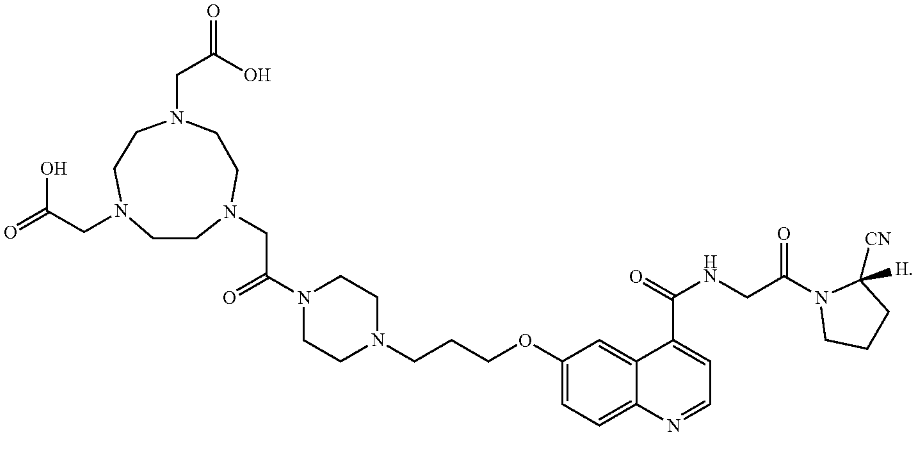

In other words, in this embodiment, the compound of general formula (I) can be regarded as compound FAPI-02, FAPI-04, FAPI-21, FAPI-34, FAPI-42, FAPI-46, FAPI-52, FAPI-69, FAPI-70, FAPI-71, FAPI-72, FAPI-73, or FAPI-74 with an albumin binding unit AB inserted into the molecular structure thereof. Compounds FAPI-02, FAPI-04, FAPI-21, FAPI-34, FAPI-42, FAPI-46, FAPI-52, FAPI-69, FAPI-70, FAPI-71, FAPI-72, FAPI-73, and FAPI-74 are disclosed as FAP inhibitors in WO2019154886A1.

In a preferred embodiment, the unit FAPI and the unit C in the compound of general formula (I) satisfy the following conditions: if the unit FAPI and the unit C were connected (with the albumin binding unit therebetween removed), the new compound obtained through the connection would be selected from: FAPI-04, FAPI-21 or FAPI-46. In an embodiment, the unit FAPI and the unit C in the compound of general formula (I) satisfy the following condition: if the unit FAPI and the unit C were connected (with the albumin binding unit therebetween removed), the new compound obtained through the connection would be FAPI-04.

In an embodiment, the unit AB comprises a 4-iodo-phenyl group as an end group.

In an embodiment, the unit AB is selected from
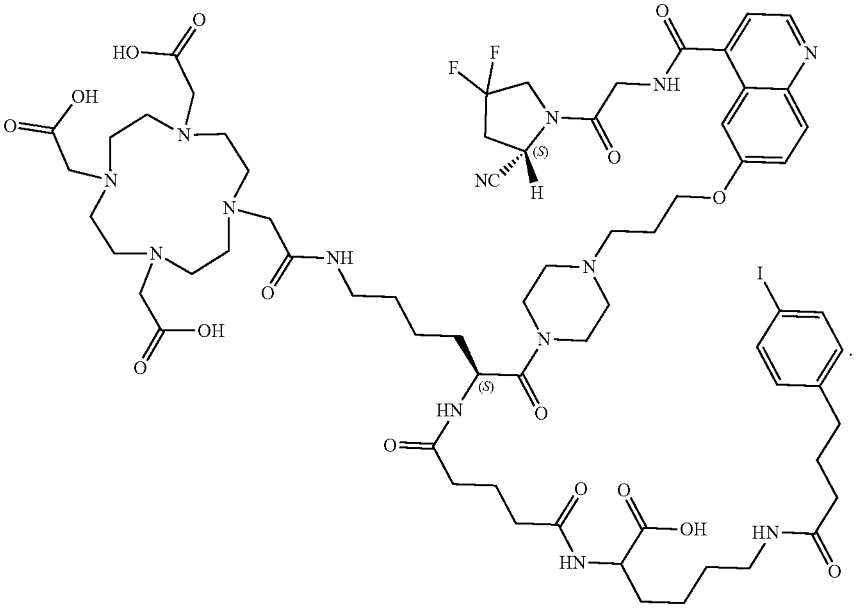
In an embodiment, the unit AB is connected to the unit by forming an amide bond with
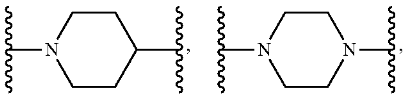
-continued
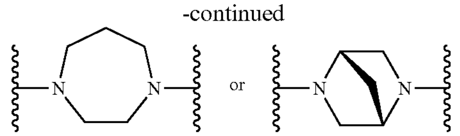
at an end of the unit FAPI, and the unit AB is connected to the unit C by forming an amide bond with a carbonyl group at an end of the unit C.
In an embodiment, the compound of general formula (I) is:
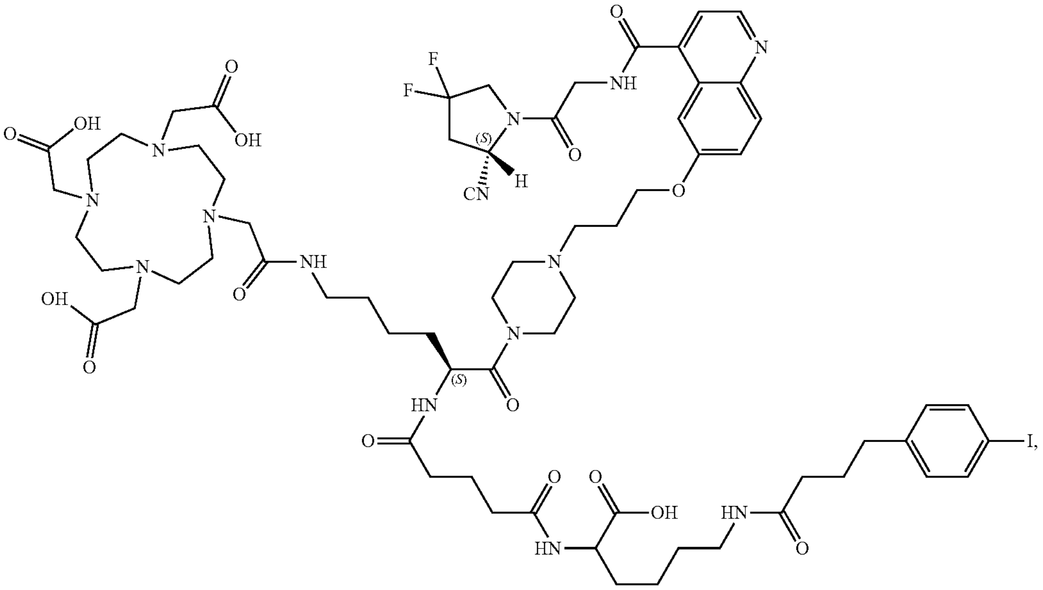
TEFAPI-06 or a pharmaceutically acceptable salt, an isomer or a solvate thereof.

Based on the small molecule FAP inhibitor (FAPI) with high affinity that is designed by Jansen et al., Loktev et al. first developed radiotracers FAPI-01 and FAPI-02, which can rapidly bind with the FAP for intake in human and murine cells. A very small amount of radiotracers are accumulated in normal tissues and are cleared fast, and therefore, high contrast can be obtained for PET imaging. In addition, FAPI-02 can be rapidly cleared from the organism through renal clearance without being retained in the renal parenchyma, which facilitates therapeutic applications. To optimize uptake and tracer retention in tumors, a series of compounds based on FAPI-02 have been developed. PET imaging of FAPI-04 shows higher tumor uptake and longer residence time, without significant increase in activity in normal organs. PET imaging of FAPI-04 was performed on patients with 28 different cancers in a clinical trial, and it was shown that only the cancer sites had uptake and normal tissues had almost no uptake, showing an excellent cancer targeting property. Such diagnostic reagent has been applied clinically at present. Because a FAP target is still an excellent therapeutic target, for patients with advanced metastatic disease, conventional methods such as surgery, radiotherapy and chemotherapy cannot inhibit tumor development or prolong patient's life. Using FAP inhibitors to carry radioactive therapeutic nuclides is a promising treatment. Therefore, it is expected to solve the problem of short circulation time of FAP inhibitor small molecules on the premise of retaining its excellent targeting properties.

TEFAPI-06 is obtained by introducing 4-(p-iodophenyl) butyric acid derivative structure into the structure of FAPI-04. The introduction of such iodobenzene structure with high affinity for albumin into the FAPI-04 structure prolongs blood circulation time of the fibroblast activation protein (FAP) inhibitor in the body, and facilitates specific high uptake at the tumor site. After an imaging metabolic rule of such structure was tested via PET imaging, it was found that the blood half-life was extended from 26 minutes to 400 minutes. In the lutetium-177 radiotherapy test, the tumor in mice is significantly inhibited. TEFAPI-06 is expected to be used in imaging and radioactive nuclide carrier for various cancers.

The present disclosure further provides a chelate, comprising:

the above compound of general formula (I) or a pharmaceutically acceptable salt, an isomer or a solvate thereof; and a radioactive nuclide.

In the chelate, a chelator unit is directly chelated with the radioactive nuclide (for example, $^{68}$Ga is chelated with a chelator unit derived from DOTA), or the radioactive nuclide is introduced indirectly via chelation with a metal (for example, $Al^{3+}$ is chelated with a chelator unit derived from DOTA, and radioactive nuclide $^{18}$F is introduced into the chelate in the form of a counterion).

In an embodiment, the radioactive nuclide is selected from $^{18}$F, $^{51}$Cr, $^{67}$Ga, $^{68}$Ga, $^{111}$In, $^{99}$mTc, $^{186}$Re, $^{188}$Re, $^{139}$La, $^{140}$La, $^{175}$Yb, $^{15}$3Sm, $^{166}$Ho, $^{86}$Y, $^{88}$Y, $^{90}$Y, $^{149}$Pm, $^{165}$Dy, $^{169}$Er, $^{177}$Lu, $^{47}$Sc, $^{142}$Pr, $^{159}$Gd, $^{212}$Bi, $^{213}$Bi, $^{72}$As, $^{72}$Se, $^{97}$Ru, $^{109}$Pd, $^{105}$Rh, $^{101m}$Rh, $^{119}$Sb, $^{128}$Ba, $^{123}$I, $^{124}$I, $^{131}$I, $^{197}$Hg, $^{211}$At, $^{151}$Eu, $^{153}$Eu, $^{169}$Eu, $^{201}$Tl, $^{203}$Pb, $^{212}$Pb, $^{64}$Cu, $^{67}$Cu, $^{188}$Re, $^{186}$Re, $^{198}$Au, $^{225}$Ac, $^{227}$Th and $^{199}$Ag. For example, the radioactive nuclide is $^{68}$Ga, $^{86}$Y or $^{177}$Lu.

The present disclosure further provides a pharmaceutical composition, comprising or consisting of:

at least one of the above chelates; and optionally, a pharmaceutically acceptable excipient.

In an embodiment, the pharmaceutical composition comprises or consists of at least one of the above chelates. In another embodiment, the pharmaceutical composition comprises or consists of at least one of the above chelates and a pharmaceutically acceptable excipient.

The composition of the present disclosure may, as necessary or as required, also contain a pharmaceutically acceptable excipient for preparing chelates for the intended route of administration. The excipient includes, but is not limited to, a diluent, a disintegrant, a precipitation inhibitor, a surfactant, glidant, a binder, a lubricant, or a coating material. The excipient is generally described in "Remington's Pharmaceutical Sciences" by E. W. Martin. Examples of the excipient include, but are not limited to, aluminum monostearate, aluminum stearate, carboxymethylcellulose, sodium carboxymethylcellulose, crospovidone, glyceryl isostearate, glyceryl monostearate, hydroxyethyl cellulose, hydroxy methyl cellulose, hydroxy octacosyl hydroxystearate, hydroxy propyl cellulose, hydroxy propyl methyl cellulose, lactose, lactose monohydrate, magnesium stearate, mannitol, microcrystalline cellulose and the like.

Reagents that may be used to formulate the composition as appropriate for the intended route of administration include:

an acidifying agent (examples include, but are not limited to, acetic acid, citric acid, fumaric acid, hydrochloric acid and nitric acid);

an alkalinizing agent (examples include, but are not limited to, aqueous ammonia, ammonium carbonate, diethanolamine, monoethanolamine, potassium hydroxide, sodium borate, sodium carbonate, sodium hydroxide, triethanolamine and trolamine); and a buffer (examples include, but are not limited to, potassium metaphosphate, dipotassium hydrogenphosphate, sodium acetate, anhydrous sodium citrate and sodium citrate dihydrate); etc.

As disclosed in WO2019154886A1, a chelate or composition containing a FAPI series compound and a radioactive nuclide can be used to diagnose or treat a disease characterized by overexpression of fibroblast activation protein in a mammal or human. In the present disclosure, by introducing an albumin binding unit into the structure of the FAPI compound disclosed in WO2019154886A1, the excellent FAP targeting property of the FAPI inhibitor is retained while the circulation time thereof is prolonged.

Another aspect of the present disclosure further relates to use of the above chelate or the composition for diagnosis or treatment of a disease characterized by overexpression of fibroblast activation protein in a mammal or human. For example, the disease characterized by the overexpression of the fibroblast activation protein (FAP) is selected from cancer, chronic inflammation, atherosclerosis, fibrosis, tissue remodeling and keloidosis, and preferably, the cancer is selected from breast cancer, pancreatic cancer, small intestine cancer, colon cancer, rectal cancer, lung cancer, head and neck cancer, ovarian cancer, hepatocellular carcinoma, esophageal cancer, hypopharyngeal cancer, nasopharyngeal cancer, laryngeal cancer, myeloma cells, bladder cancer, cholangiocarcinoma, clear cell renal carcinoma, neuroendocrine tumor, carcinogenic osteomalacia, sarcoma, CUP (carcinoma of unknown primary), thymic carcinoma, glioma, neuroglioma, astrocytoma, cervical cancer and prostate cancer.

A still another aspect of the present disclosure relates to a kit, comprising or consisting of the above chelate or pharmaceutical composition, and an instruction for diagnosing or treating a disease. In a preferred embodiment, the disease is the above disease characterized by the overexpression of fibroblast activation protein.

EXAMPLES

The starting materials in the examples are commercially available and/or can be prepared in various methods well known to persons skilled in the art of organic synthesis. Persons skilled in the art of organic synthesis will appropriately select the reaction conditions (including the solvent, reaction atmosphere, reaction temperature, duration of the experiment, and a post-treatment) in the following synthesis methods. Persons skilled in the art of organic synthesis understand that the functional group(s) on each part of a molecule should be compatible with the proposed reagent and reaction.

Abbreviations:

I. Chemical Synthesis of TEFAPI-06

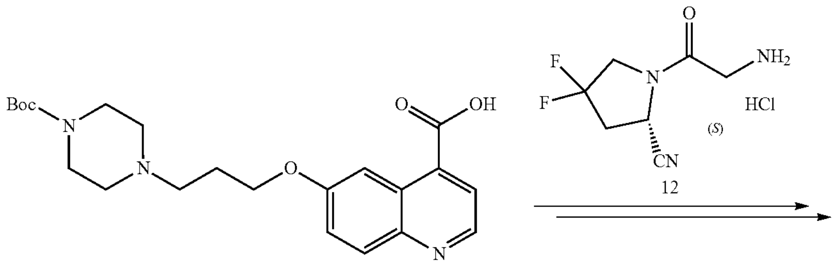

18

12

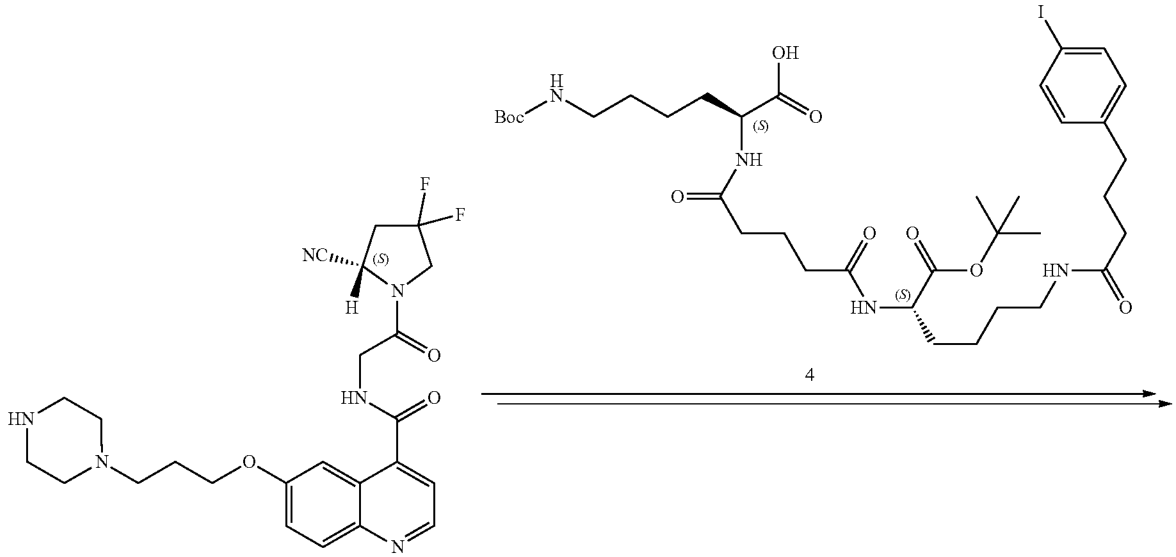

20

4

-continued

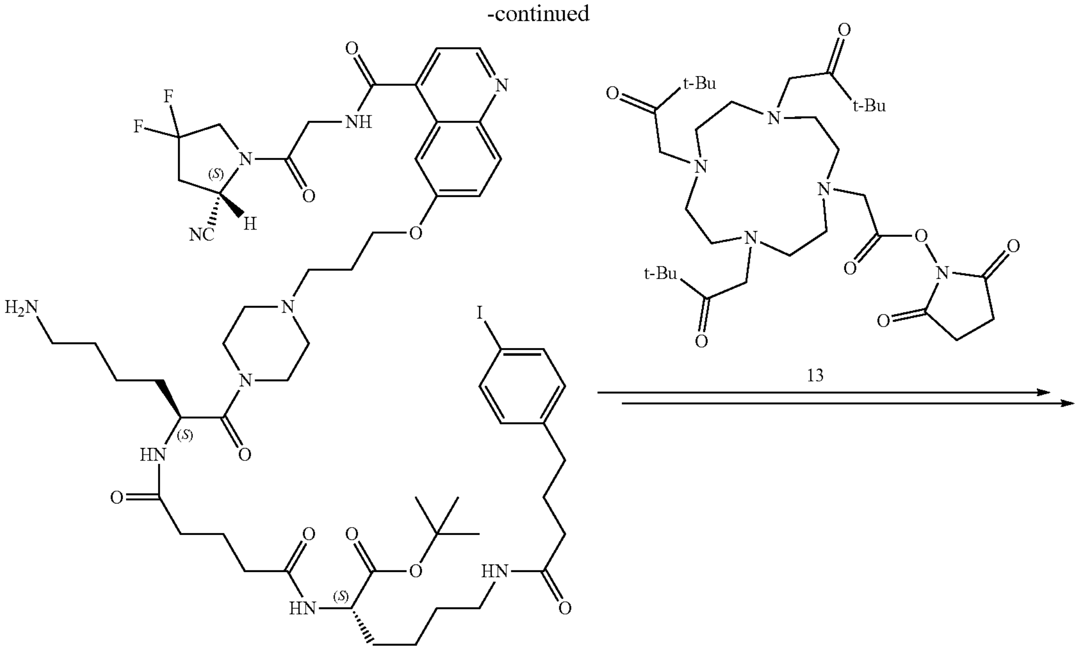

22

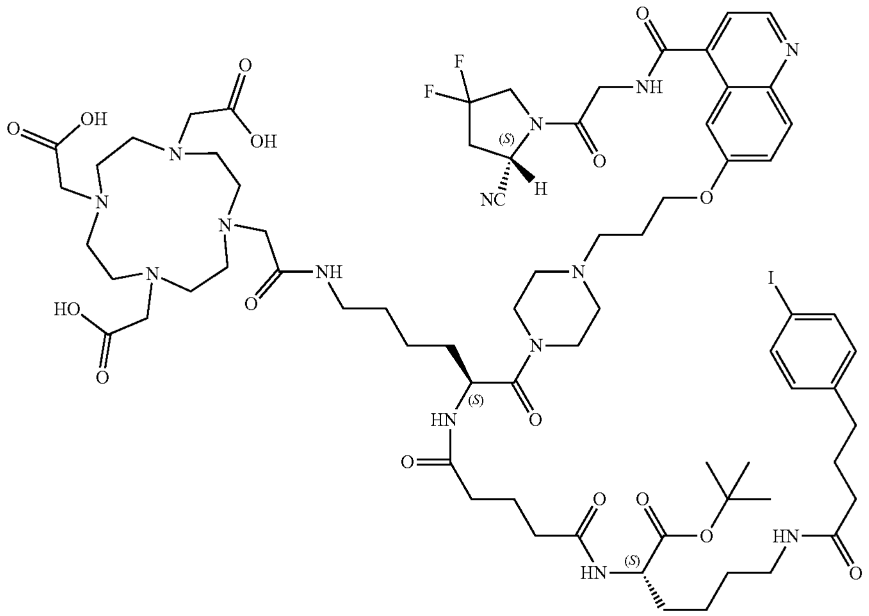

24 (TEF API-06)

All reagents and compounds synthesized are generally commercially available in China. Suppliers include Sinopharm Chemical Reagent Co., Ltd., Saen Chemical Technology (Shanghai) Co., Ltd., Jiuding Chemical (Shanghai) Technology Co., Ltd., J&K Scientific Co., Ltd., Beijing Tongguang Fine Chemicals Company, Bide Pharmatech Co., Ltd., Beijing InnoChem Science & Technology Co., Ltd., Shanghai Macklin Biochemical Co., Ltd., and Sigma-Aldrich (Shanghai) Trading Co., Ltd. CAS numbers of key starting materials are all marked on a route map.

TEFAPI-06 was synthesized via the above chemical route. Specifically, TEFAPI-06 can be divided into five parts: synthesis of block 4, synthesis of block 12, synthesis of block 13, synthesis of block 20, and block connection, and there is a specific prerequisite therebetween.

Synthesis of Block 4

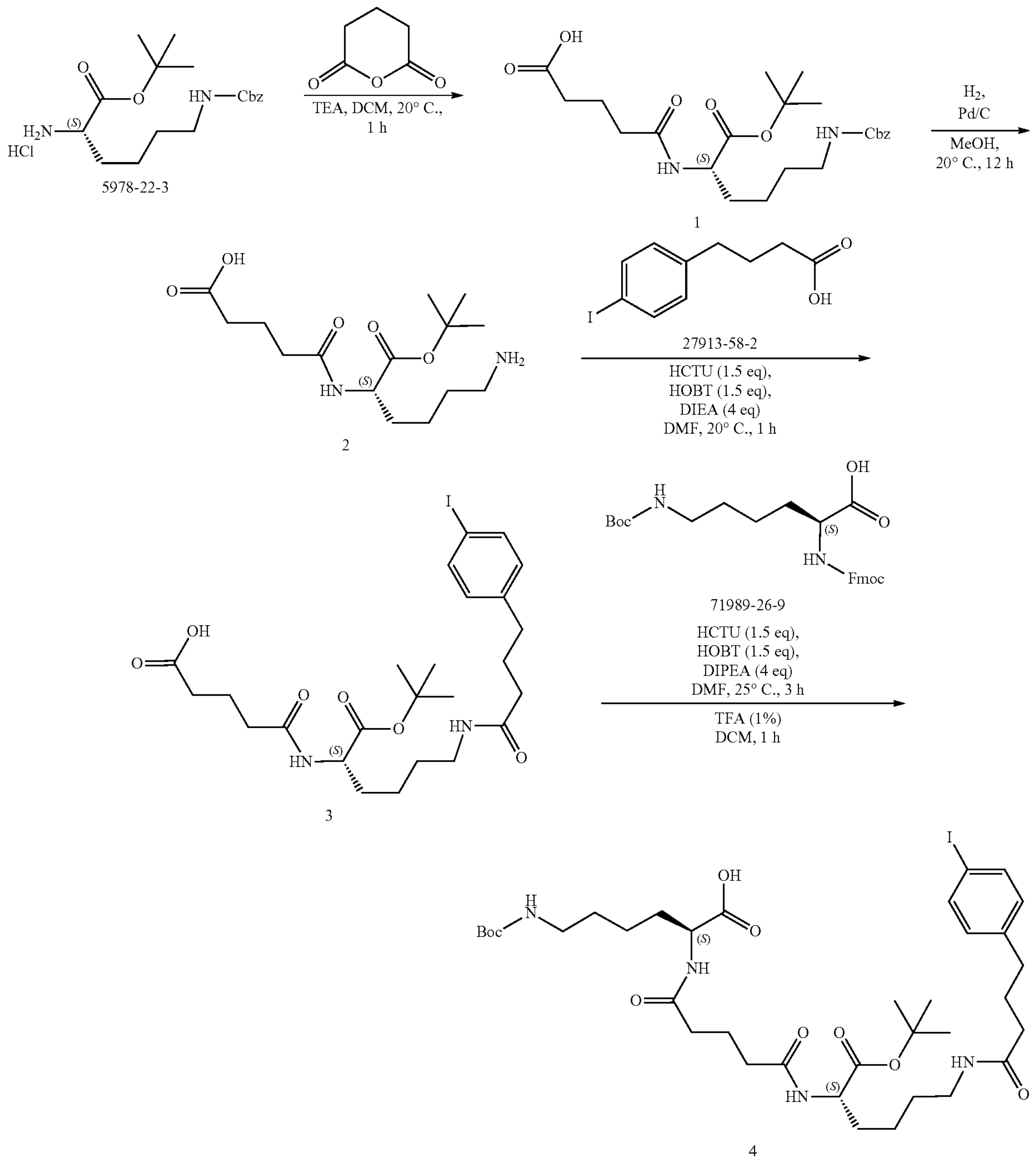

5978-22-3

1

27913-58-2

2

71989-26-9

3

4 a) Tetrahydropyran-2,6-dione (9.18 g, 80.45 mmol, 1.5 eq) was added to a solution of compound 5978-22-3 (20 g, 53.64 mmol, 1 eq, HCl) in dichloromethane (200 mL), then the solution was cooled to 0° C., then triethylamine (16.28 g, 160.91 mmol, 22.40 mL, 3 eq) was added dropwise and then stirred at 20° C. for reaction for 1 hour. After the reaction ended, the solution was concentrated to obtain a colorless oily liquid compound 1 (20 g, crude product). MS(ESI$^+$): m/z 451.2 $(M+H)^+$ b) Pd/C (8 g, purity: 10%) was added to a solution of the compound 1 (20 g, 44.39 mmol, 1 eq) in methanol (200 mL), followed by reaction in $H_2$ (15 psi) atmosphere for 12 hours. After the reaction ended, the solution was concentrated under reduced pressure to obtain a colorless oily liquid compound 2 (14 g, crude product). MS(ESI$^+$): m/z 317.2 $(M+H)^+$ c) 1-hydroxypyrrolidine-2,5-dione (6.55 g, 56.88 mmol, 1.1 eq) and dicyclohexylcarbodiimide (12.80 g, 62.05 mmol, 12.55 mL, 1.2 eq) were added to a solution of compound 27913-58-2 (15 g, 51.71 mmol, 1 eq) in dichloromethane (150 mL) at 0° C., and then the solution was warmed to room temperature, followed by reaction for 1 hour. After the reaction ended, a filtrate was obtained via filtering and concentrated under reduced pressure to obtain a light yellow solid, and the light yellow solid was then dissolved in dimethylformamide (120 mL). The compound 2 (12 g, 37.93 mmol, 1 eq) and N,N-diisopropylethylamine (14.71 g, 113.78 mmol, 19.82 mL, 3 eq) were added, followed by reaction at room temperature for 2 hours. The reaction mixture was concentrated and then purified via prep-HPLC to obtain a colorless oily liquid compound 3 (10 g, 16.57 mmol, yield: 43.68%, purity: 97.5%). MS(ESI$^+$): m/z 533.1 $(M/2+H)^+$ d) Compound 71989-26-9 (42.90 g, 91.56 mmol, 1.2 eq) and N,N-diisopropylethylamine (29.58 g, 228.90 mmol, 39.87 mL, 3 eq) were added to Trt-Cl resin (3.85 g, 76.3 mmol, 1 eq)/dichloromethane (500 ml) solution, stirred at room temperature and bubbled with nitrogen for 48 hours. Then the mixture was washed successively with dichloromethane (5×500 mL), $CH_{30}H$ (5×500 mL) and dimethylformamide (5×500 mL). Then piperidine/dimethylformamide (v/v=1:5, 400 mL) solution was added, and the resulting mixture was bubbled with nitrogen for 20 minutes, and then washed with dimethylformamide (5×300 mL). Then dimethylformamide (300 mL) was added, the reaction was cooled to 0° C., compound 3 (18.14 g, 30.43 mmol, 1.1 eq), 6-chlorobenzotriazole-1,1,3,3-tetramethyluronium hexafluorophosphate HCTU (22.84 g, 56.96 mmol, 2 eq), 1-hydroxybenzotriazole HOBT (1.92 g, 14.14 mmol, 0.5 eq) and N,N-diisopropylethylamine (10.8 g, 86.44 mmol, 14.9 mL, 3 eq) were added successively, and then the resulting mixture was warmed to room temperature, followed by reaction for 2 hours. Then the resulting mixture was washed with dimethylformamide (4×400 mL) and dichloromethane (4×400 mL), then dichloromethane/trifluoroacetic acid (v/v=100:1, 600 mL) was added, and the resulting mixture was bubbled and reacted for 20 minutes and filtered. The filtrate was adjusted to neutrality with $NaHCO_3$(aq), and separated and extracted with dichloromethane (200 mL×3) and water (200 mL×3), and a combined organic phase was washed with citric acid (200 mL×3), and then dried by evaporation under reduced pressure to obtain a yellow solid compound 4 (6 g, 7.11 mmol, yield: 74.99%, purity: 96.77%). $^1$H NMR (400 MHz, $CDCl_3$) δ=1.30-1.40 (m, 2H), 1.43-1.51 (m, 24H), 1.91-1.93 (m, 6H), 2.16-2.21 (m, 7H), 2.56-2.60 (m, 3H), 3.07-3.11 (m, 3H), 3.47-3.49 (m, 1H), 4.48-4.50 (m, 1H), 4.57-4.60 (m, 1H), 4.76-4.79 (m, 1H), 5.86 (br s, 1H), 6.90-6.94 (m, 2H), 7.58-7.61 (m, 2H), 7.88-7.91 (m, 1H), 8.09-8.12 (m, 1H). MS(ESI$^+$): m/z 817.4 $(M+H)^+$ Synthesis of Block 12

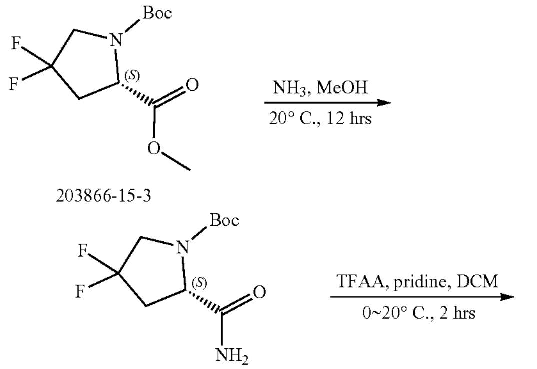

203866-15-3

8

-continued

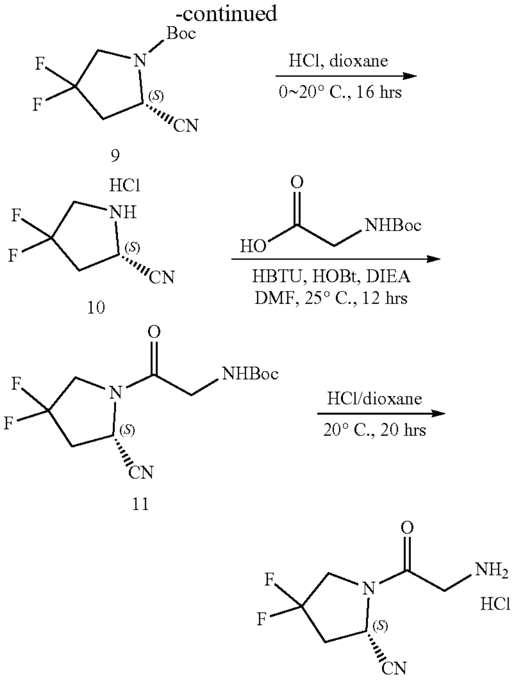

9

10

11

12 a) A solution of $NH_3$ (28.89 g, 1.70 mol, 45 eq) in MeOH (25 mL) was slowly added to a solution of compound 203866-15-3 (10 g, 37.70 mmol, 1 eq) in MeOH (125 mL) over 20 minutes at 0° C. Then the temperature was warmed to room temperature, and the resulting mixture was stirred for reaction for 18 hours under $N_2$ (15 psi) atmosphere. After the reaction ended, the resulting mixture was concentrated by evaporation under reduced pressure and slurried with PE/MTBE to obtain a yellow solid compound 8 (8.9 g, 35.57 mmol, yield: 94.34%). $^1$H NMR (400 MHz DMSO): δ 1.28-1.45 (m, 9H), 2.16-2.38 (m, 1H), 2.59-2.87 (m, 1H), 3.55-3.84 (m, 2H), 4.08-4.36 (m, 1H), 6.97-7.19 (m, 1H), 7.36-7.61 (m, 1H)

b) Pyridine (3.38 g, 42.68 mmol, 3.44 mL, 1.2 eq) was slowly added to a solution of compound 8 (8.9 g, 35.57 mmol, 1 eq) in dichloromethane (100 mL) over 20 minutes at 0° C. The resulting mixture was maintained at 0° C., trifluoroacetic anhydride (8.96 g, 42.68 mmol, 5.94 mL, 1.2 eq) was added, then the resulting mixture was warmed to room temperature and stirred for 18 hours for reaction, and then concentrated under reduced pressure. The resulting mixture was slurried by using PE/MTBE to obtain a yellow solid compound 9 (7.5 g, 32.30 mmol, yield: 90.81%). $^1$H NMR (400 MHz chloroform-d): δ 1.33-1.66 (m, 9H), 2.71 (br t, J=9.04 Hz, 2H), 3.80 (br s, 2H), 4.52-4.90 (m, 1H)

c) HCl/dioxane (4 M, 14.00 mL, 1.86 eq) was added to a solution of compound 9 (7.0 g, 30.14 mmol, 1 eq) in acetonitrile (200 mL), followed by reaction for 18 hours. A solid was obtained via filtering and washed with MTBE (100 mL) to obtain a white solid compound 10 (2.2 g, 13.05 mmol, yield: 43.30%, HCl). $^1$H NMR (400 MHz DMSO) δ 2.64-3.13 (m, 2H), 3.48-3.89 (m, 2H), 4.99 (br t, J=6.95 Hz, 1H), 9.80 (br s, 2H)

d) 2-(tert-butoxycarbonylamino)acetic acid (779.41 mg, 4.45 mmol, 1.5 eq), 1-hydroxybenzotriazole HOBT (80.16 mg, 593.22 umol, 0.2 eq), 2-(IH-benzotriazol-1-yl)-N,N,N',N'-tetramethylisourea phosphorus hexafluoride HBTU (2.25 g, 5.93 mmol, 2 eq) and compound 10 (500 mg, 2.97 mmol, 1 eq, HCl) were added in sequence to 10 ml of dimethylformamide, followed by reaction and stirring for 30 minutes. Then N,N-diisopropylethylamine (1.15 g, 8.90 mmol, 1.55 mL, 3 eq) was added and stirred for 16 hours. After the reaction ended, water (20 mL) was added and the resulting mixture was extracted with ethyl acetate (50 mL). After the organic phase was concentrated, the organic phase was purified via silica gel column chromatography (PE:ethyl acetate=1:1) to obtain compound 11 (0.625 g, 2.13 mmol, yield: 71.68%). $^1$H NMR (400 MHz DMSO): δ 1.38 (m, 9H), 2.78 (m, 2H), 3.77 (m, 2H), 4.06 (m, 1H), 4.23 (m, 1H), 5.07 (d, J=5.2 Hz, 1H), 7.14 (m, 1H)

e) HCl/dioxane (4 M, 2.67 mL, 7.71 eq) was added to a solution of compound 11 (0.4 g, 1.38 mmol, 1 eq) in acetonitrile (13.5 mL) at 0° C., and then the mixture was warmed to room temperature and reacted for 16 hours. The resulting mixture was concentrated to obtain an off-white solid compound 12 (322 mg, 1.28 mmol, yield: 92.89%, purity: 90%, HCl). $^1$H NMR (400 MHz DMSO): δ 2.81-3.01 (m, 2H), 3.57 (s, 2H), 3.69 (br d, J=5.01 Hz, 1H), 3.78-3.89 (m, 1H), 3.91-4.14 (m, 2H), 4.24 (ddd, J=15.59, 11.41, 4.11 Hz, 1H), 5.19 (dd, J=8.70, 3.34 Hz, 1H), 8.38 (br s, 3H)

Synthesis of Block 13

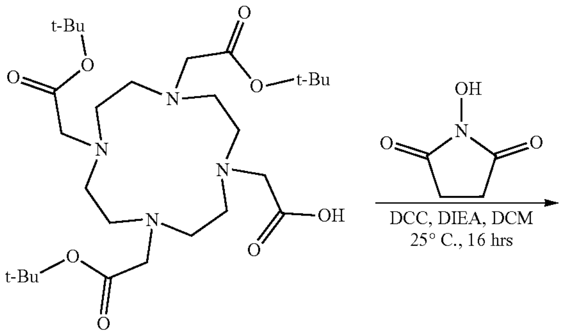

137076-54-1

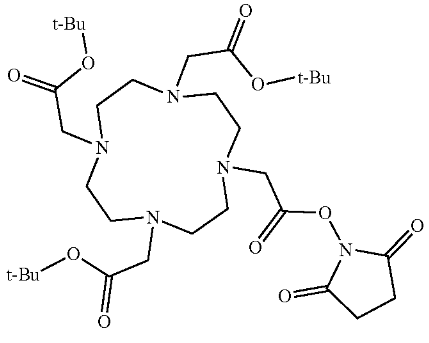

13 a) Compound 137076-54-1 (150 mg, 261.90 μmol, 1 eq) was dissolved in acetonitrile (15 mL), 1-hydroxypyrrolidine-2,5-dione (33.16 mg, 288.09 μmol, 1.1 eq) and HBTU (109.26 mg, 288.09 μmol, 1.1 eq) were added in sequence, and the mixture was stirred for 12 hours, and then the mixture was dried under reduced pressure and purified by prep-TLC (EA:CAN=7:1) to obtain a pale yellow solid compound 13 (115 mg, 171.69 umol, yield: 65.56%) for direct use in the next step.

Synthesis of Block 20

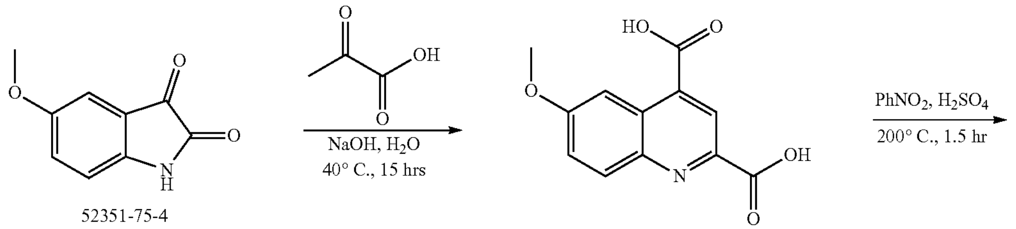

52351-75-4

14

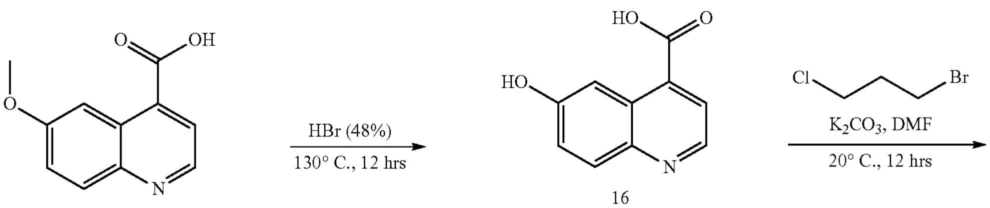

15

16

-continued

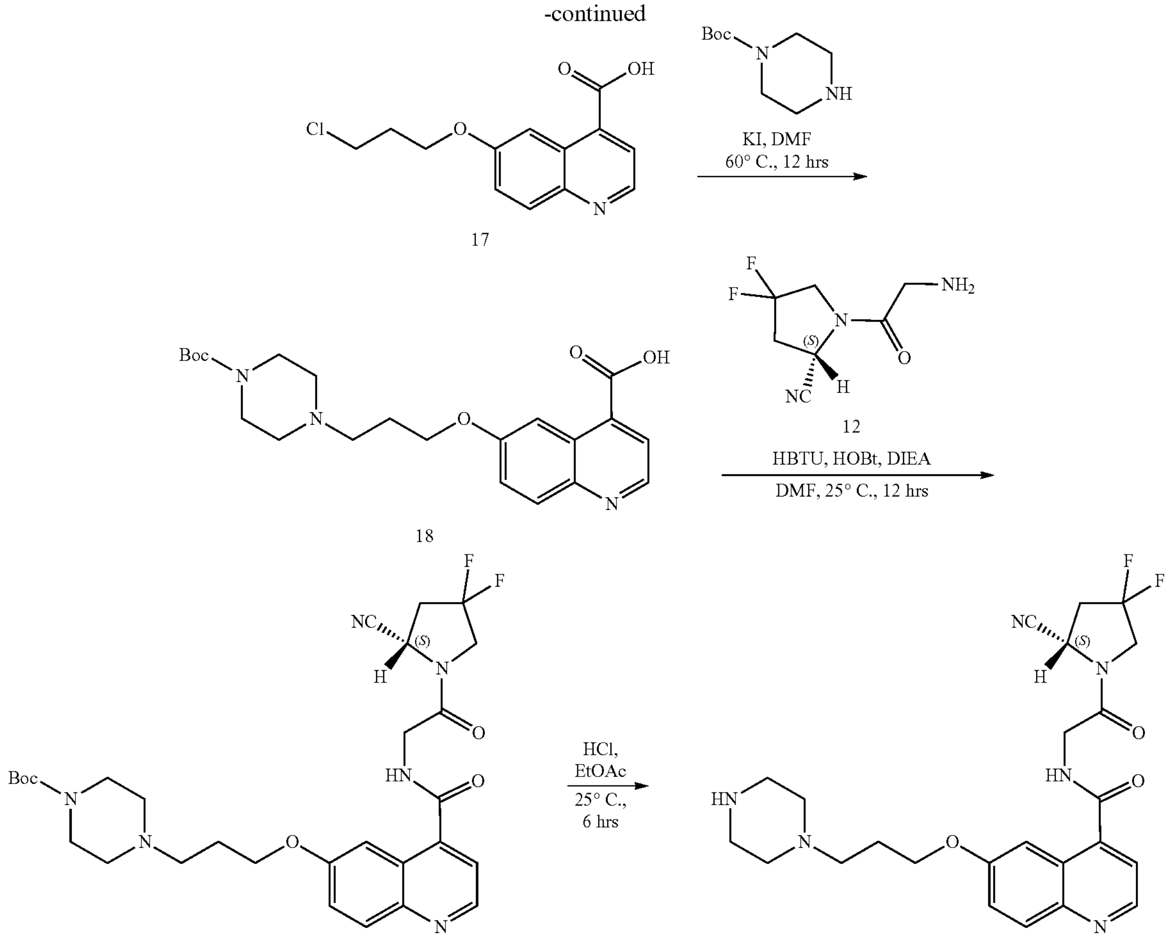

17 18 12 19 20 a) Compound 52351-75-4 (20 g, 112.89 mmol, 1 eq) and KOH (69.68 g, 1.24 mol, 11 eq) were dissolved in $H_2O$ (200 mL), then pyruvic acid (10.94 g, 124.18 mmol, 8.75 mL, 1.1 eq) was added, and the reaction mixture was reacted at 40° C. for 15 hours. The mixture was then cooled to 15° C., and acidified to pH 3 with hydrochloric acid, the solid was obtained via filtering and washed with deionized water to obtain an off-white solid compound 14 (24 g, 92.23 mmol, yield: 81.70%, purity: 95%) $^1$H NMR (400 MHz DMSO): δ 3.70-4.24 (m, 3H), 7.58 (dd, J=9.24, 2.80 Hz, 1H), 8.15 (d, J=9.30 Hz, 1H), 8.26 (d, J=2.74 Hz, 1H), 8.53 (s, 1H), 13.75 (br s, 2H), MS (ESI+): m/z 248.1 (M+H)+ b) Nitrobenzene (150 mL) was added to compound 14 (24 g, 97.09 mmol, 1 eq) and the mixture was stirred at 220° C. for 1.5 hours. The mixture was then cooled to 15° C., PE (150 mL) was added, and the precipitated solid was washed with PE (100 mL) to obtain an off-white solid compound 15 (16.8 g, 82.68 mmol, yield: 85.16%). $^1$H NMR (400 MHz DMSO) δ 3.72-4.14 (m, 3H), 7.49 (dd, J=9.23, 2.75 Hz, 1H), 7.93 (d, J=4.40 Hz, 1H), 8.02 (d, J=9.17 Hz, 1H), 8.18 (d, J=2.69 Hz, 1H), 8.87 (d, J=4.40 Hz, 1H), 13.76 (br s, 1H). MS ($ESI^+$): m/z 202.1 $(M-H)^-$ c) Hydrogen bromide (1 L, 48% aqueous solution) was added to compound 15 (40 g, 196.86 mmol, 1 eq), and the mixture was stirred at 130° C. for 12 hours. Then, for the reaction, 350 mL of 30% sodium hydroxide solution was added for basification to pH=6, and a large amount of precipitate was obtained. After the precipitate was obtained via filtering, the precipitate was washed with methanol and dried via suction to obtain a crude product, and the crude product was washed several times with methanol to obtain a product of a brown solid compound 16 (30 g, 128.93 mmol, yield: 65.50%, purity: 81.3%). $^1$H NMR (400 MHz, DMSO-$d_6$) δ ppm 13.66 (br s, 1H), 10.24 (s, 1H), 8.77 (d, J=4.5 Hz, 1H), 8.06 (d, J=2.6 Hz, 1H), 7.95 (d, J=9.1 Hz, 1H), 7.84 (d, J=4.4 Hz, 1H), 7.36 (dd, J=2.7, 9.1 Hz, 1H). MS($ESI^-$): m/z 377.0 $(2M-H)^-$ d) Potassium carbonate (87.67 g, 634.36 mmol, 4 eq) and 1-bromo-3-chloro-propane (24.97 g, 158.59 mmol, 15.60 mL, 1 eq) were added to a solution of compound 16 (30 g, 158.59 mmol, 1 eq) in dimethylformamide (300 mL), and then the resulting mixture was reacted and stirred at 60° C. for 12 hours. After evaporating and concentrating, 200 mL of water was added to the system, a large amount of solid was precipitated, and then the reaction mixture was stirred at 25° C. for 15 minutes, and filtered via suction. The solid was ground with ethyl acetate and filtered to obtain a brown solid compound 17 (37.58 g, 130.13 mmol, yield: 86.15%, purity: 92%). $^1$H NMR (400 MHz, DMSO-$d_6$) δ ppm 2.26-2.98 (m, 2H), 3.83-3.88 (m, 2H), 4.22-4.25 (m, 2H), 7.54 (dd, J=9.19, 2.69 Hz, 1H), 7.96 (d, J=4.38 Hz, 1H), 8.03-8.11 (m, 1H), 8.19 (d, J=2.63 Hz, 1H), 8.90 (d, J=4.38 Hz, 1H). MS($ESI^+$): m/z 266.1 $(M+H)^+$, e) The compound 17 (30 g, 112.91 mmol, 1 eq) was added to N-methylpyrrolidone (300 mL), and tert-butyl piperazine- 1-carboxylate (105.15 g, 564.56 mmol, 5 eq) and potassium iodide were added (9.37 g, 56.46 mmol, 0.5 eq), and then the reaction mixture was stirred at 60° C. for 12 hours. The reaction mixture was cooled to room temperature and filtered, and the crude product was purified by Prep-HPLC (0.1% FA) to obtain a yellow solid compound 18 (42.96 g, 96.16 mmol, yield: 85.16%, purity: 93%). $^{1}H$ NMR (400 MHz, DMSO-$d_6$) δ ppm 8.82 (d, J=4.4 Hz, 1H), 8.19-8.16 (m, 1H), 7.99 (d, J=9.3 Hz, 1H), 7.85 (d, J=4.4 Hz, 1H), 7.45 (dd, J=2.8, 9.1 Hz, 1H), 4.15 (br t, J=6.2 Hz, 2H), 2.62-2.50 (m, 6H), 2.42 (br t, J=4.6 Hz, 4H), 1.99 (br d, J=6.6 Hz, 2H), 1.39 (s, 9H). MS(ESI$^+$): m/z 416.1 $(M+H)^+$ f) O-benzotriazol-1-yl-tetramethyluronium hexafluoro phosphate (19.76 g, 52.10 mmol, 2 eq), 1-hydroxybenzotriazole (7.04 g, 52.10 mmol, 2 eq), and N,N-diisopropylethylamine (10.10 g, 78.15 mmol, 13.61 mL, 3 eq) were added to a solution of compound 18 (12.00 g, 26.57 mmol, purity: 92%, 1.02 eq) in dimethylformamide (120 mL), followed by the addition of compound 12 (5.88 g, 26.05 mmol, 1.00 eq, HCl), and the reaction mixture was reacted and stirred at 25° C. for 12 hours. The reaction mixture was filtered, the filtrate was purified by prep-HPLC (HCl) to obtain a yellow solid compound 19 (11.27 g, 17.29 mmol, yield: 66.37%, purity: 90%). $^{1}H$ NMR (400 MHz, DMSO-$d_6$) δ ppm. 1.41 (s, 9H), 2.27-2.33 (m, 2H), 3.27-3.29 (m, 5H), 3.43-3.55 (m, 2H), 3.93-4.21 (m, 10H), 5.19 (dd, J=9.26, 2.75 Hz, 1H), 7.59 (dd, J=9.26, 2.63 Hz, 1H), 7.69 (d, J=4.63 Hz, 1H) 7.87-8.00 (m, 1H), 8.14 (d, J=9.26 Hz, 1H), 8.95 (d, J=4.63 Hz, 1H), 9.24 (br t, J=5.82 Hz, 1H), 11.00 (br s, 1H). MS(ESI$^+$): m/z 587.2 $(M+H)^+$, g) The compound 19 (2 g, 3.41 mmol, 1 eq) was dissolved in ethyl acetate (40 mL), a hydrochloric acid/ethyl acetate solution (4 M, 4 mL, 4.69 eq) was added, and then the reaction mixture was reacted at 25° C. for 6 hours. The reaction mixture was concentrated by evaporation and used directly to obtain a yellow solid compound 20 (1.5 g, crude product, HCl). MS(ESI$^-$): m/z 485.1 $(M+H)^+$ Block Connection

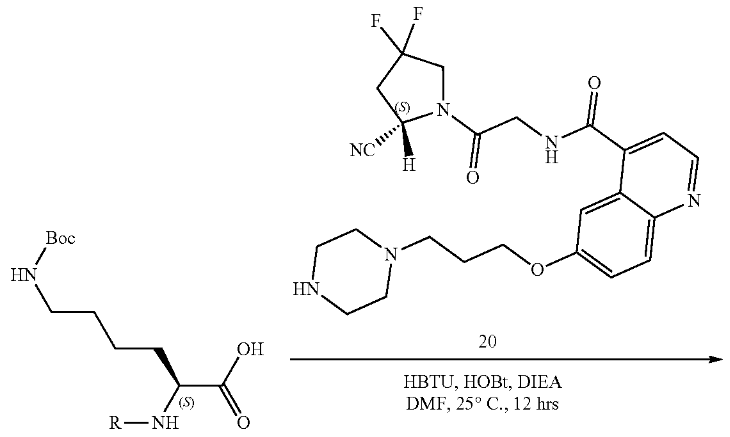

4

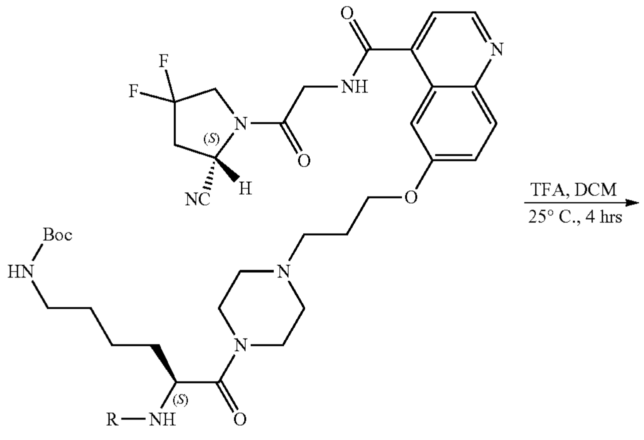

21

-continued
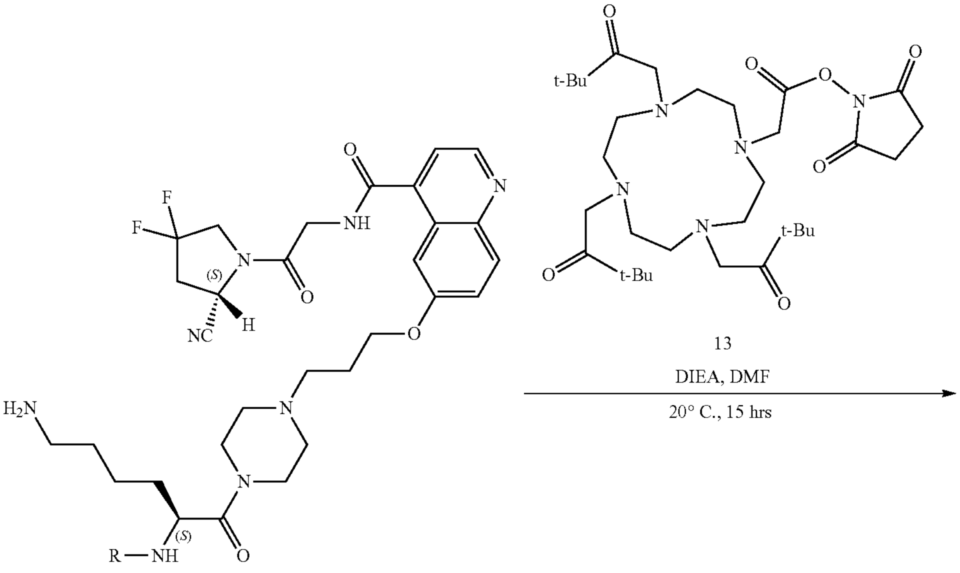
22
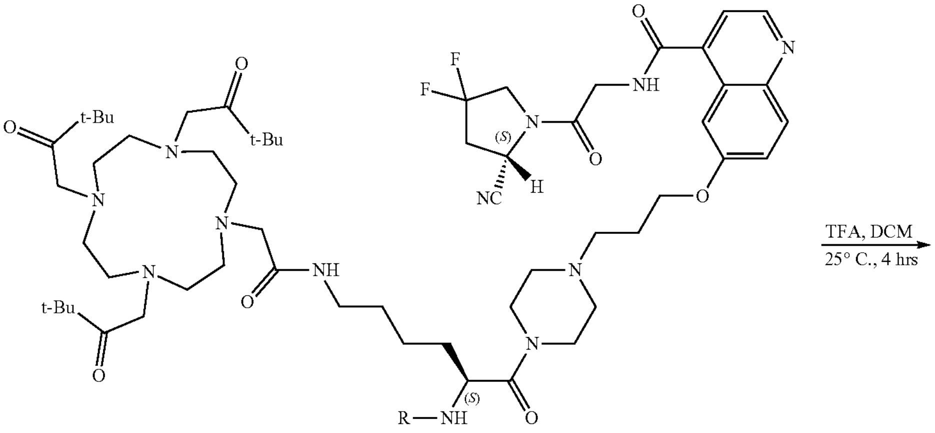
23
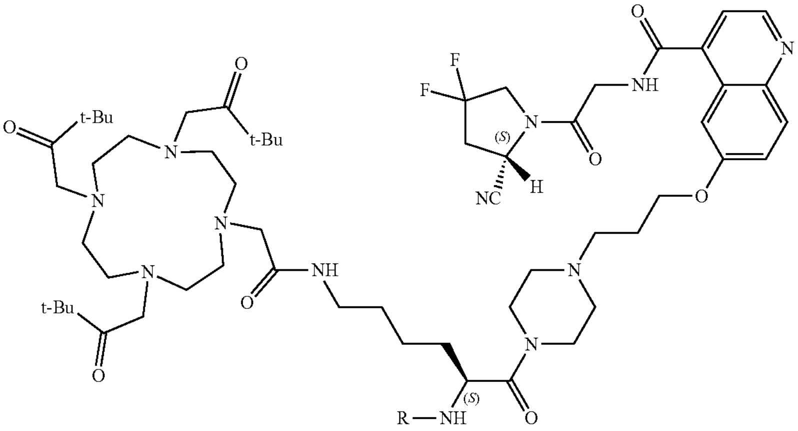
24 (TEF API-06)

-continued

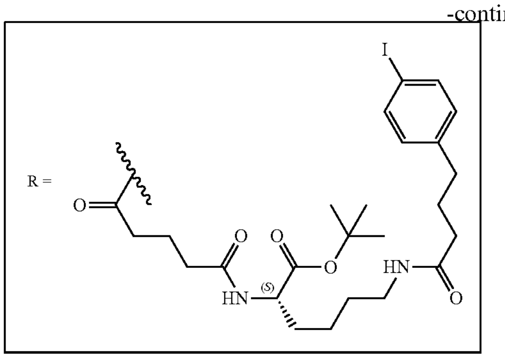

a) Compound 4 (858.97 mg, 1.05 mmol, 1.1 eq) was dissolved in dimethylformamide (5 mL), and HBTU (453.23 mg, 1.20 mmol, 1.25 eq), HOBT (167.94 mg, 1.24 mmol, 1.3 eq), N,N-diisopropylethylamine (617.83 mg, 4.78 mmol, 832.65 uL, 5 eq) and compound 20 (229.65 mg, 333.04 umol, 1 eq) were added, and the mixture was stirred for 12 hours. After the reaction product was concentrated, the reaction product was purified by prep-HPLC (HCl) to obtain white solid compound 21 (230 mg, 170.00 umol, yield: 17.78%, purity: 95%). MS($ESI^+$): m/z 1285.4 $(M+H)^+$ b) The compound 21 (150 mg, 116.71 umol, 1 eq) was dissolved in dichloromethane (10 mL), trifluoroacetic acid (3.08 g, 27.01 mmol, 2 mL, 231.45 eq) was added, and the reaction mixture was reacted and stirred for 4 hours, and then evaporated and concentrated, to directly obtain a crude product of a yellow oily liquid compound 22 (150 mg, crude product, trifluoroacetic acid). MS($ESI^+$): m/z 1129.3 $(M+H)^+$ c) The compound 22 (150 mg, 120.67 umol, 1 eq, trifluoroacetic acid) was dissolved in dimethylformamide (1.6 mL), and N,N-diisopropylethylamine (124.77 mg, 965.36 umol, 168.15 uL, 8 eq) and compound 13 (88.91 mg, 132.74 umol, 1.1 eq) were added in sequence, and the reaction mixture was reacted and stirred for 12 hours and then concentrated in vacuo to remove the solvent. A yellow oily crude product compound 23 (220 mg, crude product) was obtained. MS($ESI^+$): m/z 1684.9 $(M/2+H)^+$ d) The compound 23 (210 mg, 124.72 umol, 1 eq) was added to trifluoroacetic acid (3.23 g, 28.36 mmol, 2.10 mL, 227.41 eq) and the mixture was stirred for 3 hours. Then the reaction mixture was concentrated under reduced pressure and purified by prep-HPLC (trifluoroacetic acid) to obtain a white solid compound 24 (TEFAPI-06) (30 mg, 26.40 μmol, yield: 21.16%, purity: 100%).

The white solid compound 24 (TEFAPI-06) is characterized as follows:

LCMS($ESI^+$): m/z 758.4 1/2 $(M+2H)^+$ Rt: 1.959 min.

LC conditions: Kinetex C18 50×2.1 mm column (5 μm particle size) 1.0 ml/min

Gradient: phase A: 0.05% trifluoroacetic acid/water, phase B: 0.05% trifluoroacetic acid/acetonitrile. 0-0.40 min 5% B, 0.40-3.00 min 5-95% B, 3.00-4.00 min 95% B.

HPLC: Rt: 2.266 min.

LC conditions: Luna-C18 2.0×50 mm column (5 μm particle size), phase A: 0.05% trifluoroacetic acid/water, phase B: 0.05% trifluoroacetic acid/acetonitrile.

LC gradient: 0.00-4.90 min: 10-80% B 0.8 mL/min, 4.90-5.50 min: 0% B 1.2 mL/min.

$^1H$ NMR (400 MHz, DMSO-$d_6$)

δ ppm 9.18-9.07 (m, 1H), 8.84 (d, J=4.4 Hz, 1H), 8.49 (br s, 1H), 8.18-7.97 (m, 3H), 7.89 (br d, J=2.4 Hz, 1H), 7.78 (br t, J=5.8 Hz, 1H), 7.62 (br d, J=8.1 Hz, 2H), 7.55 (d, J=4.4 Hz, 1H), 7.46 (br dd, J=2.7 Hz, 9.1 Hz, 1H), 7.00 (br d, J=8.1 Hz, 2H), 5.15 (br dd, J=3.3, 9.0 Hz, 1H), 4.69 (br s, 1H), 4.47-4.08 (m, 6H), 4.07-3.69 (m, 13H), 3.64-3.22 (m, 11H), 3.21-2.69 (m, 14H), 2.47 (br s, 2H), 2.33-1.90 (m, 9H), 1.87-1.18 (m, 18H).

$^{19}F$ NMR (400 MHz, DMSO-$d_6$) −73.867

$^1H$ NMR (400 MHz, methanol-$d_4$)

δ ppm 8.85 (d, J=4.6 Hz, 1H), 8.22-7.97 (m, 2H), 7.71-7.53 (m, 4H), 6.99 (d, J=8.3 Hz, 2H), 5.15 (br d, J=9.3 Hz, 1H), 4.83-4.74 (m, 4H), 4.49-4.30 (m, 6H), 4.30-4.08 (m, 4H), 3.90-3.38 (m, 17H), 3.20-2.74 (m, 16H), 2.58 (s, 2H), 2.40 (br s, 2H), 2.30-2.15 (m, 6H), 2.02-1.82 (m, 6H), 1.77-0.99 (m, 11H).

$^{18}F$ NMR (400 MHz, methanol-$d_4$) −77.161

II. Determination of the Half-Life In Vivo by Imaging Healthy Mice with $^{68}$Ga-TEFAPI-06

A germanium-gallium generator was eluted with 5 mL of 0.6 M high-purity hydrochloric acid to obtain Ga-68 hydrochloric acid solution. 1 mL of the eluted Ga-68 solution was taken, 100 μL of 3M sodium hydroxide and 130 μL of 3M sodium acetate were added to adjust the acidity, the final pH was 4.0, 50 μg of TEFAPI-06 precursor was added, and the reaction mixture was heated to 90° C., and maintained at the temperature for 10 minutes. The reaction solution was passed through a C18 column to remove free ions, and then the C18 column was eluted with ethanol solution. Labeled $^{68}$Ga-TEFAPI-06 was obtained.

37 MBq labeled product was taken, 200 μL of normal saline was added for dilution, the drug was drawn with an insulin syringe for later use, and ethanol content in the drug was not higher than 5%. Healthy mice were anesthetized in advance and then placed on a PET/CT collection bed and an indwelling needle was placed at the tail vein. The syringe was attached to the indwelling needle, and collection of PET data was started at the zero moment of needle pushing. Collection time points were 0-60 min, 2 h, 3 h, 4 h, and 5 h respectively. After the collection, the data was reconstructed with professional software, and reconstruction conditions were to reconstruct the data at intervals of every minute for the first 5 minutes, reconstruct the data every 5 minutes in 5-60 minutes, and reconstruct the data at each of the other time points. The collected data was processed by PET reconstruction software to obtain continuous image. In PET processing software, a fixed region was depicted at the heart of the mouse, and SUV-Mean and SUV-Max values at the heart were obtained. The obtained SUV was simulated via data processing software. The corresponding blood half-life was obtained, and as shown in FIG. 1, the half-life of TEFAPI-06 was calculated to be 398 minutes.

Figure 2:
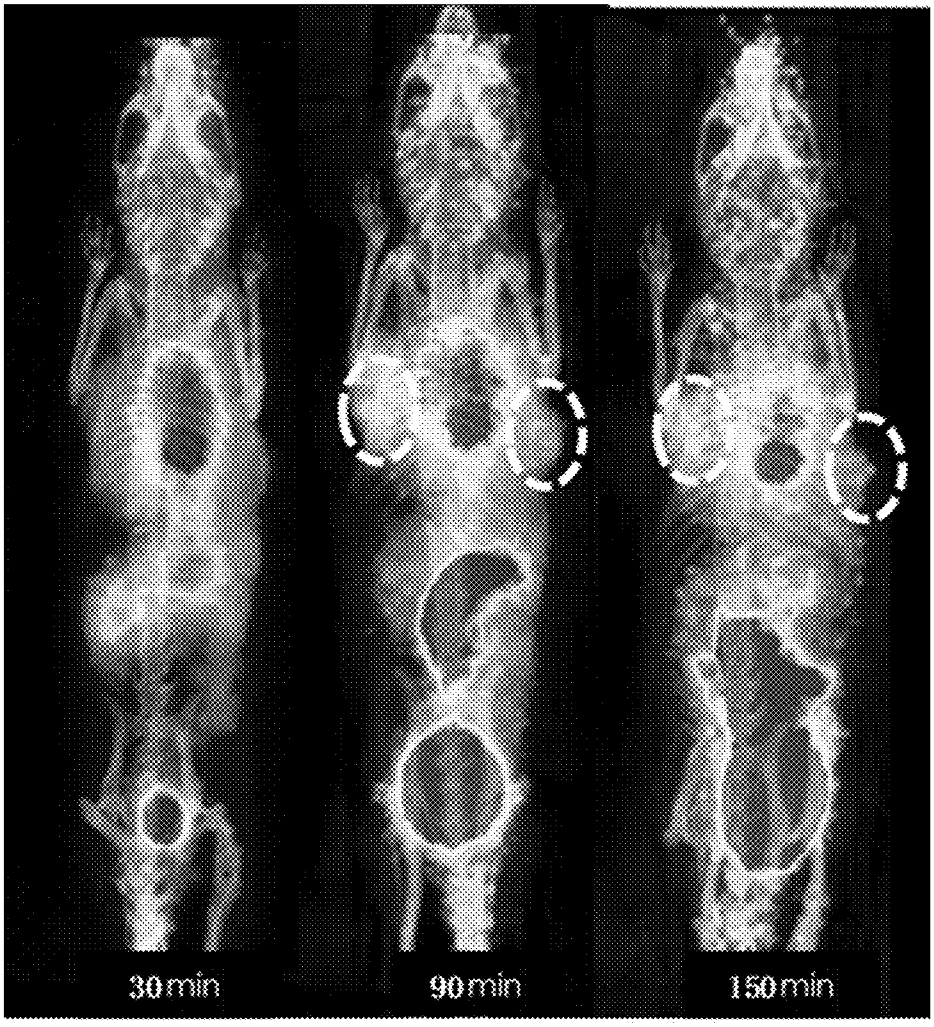
FIG. 2 shows results of PET imaging with $^{68}Ga$-TEFAPI-06 in a PDX mouse model of pancreatic cancer.

III. PET Imaging with $^{68}$Ga-TEFAPI-06 in a PDX Mouse Model of Pancreatic Cancer A germanium-gallium generator was eluted with 5 mL of 0.6 M high-purity hydrochloric acid to obtain Ga-68 hydrochloric acid solution. 1 mL of the eluted Ga-68 solution was taken, 100 μL of 3M sodium hydroxide and 130 μL of 3M sodium acetate were added to adjust acidity, the final pH was 4.0, 50 μg of TEFAPI-06 precursor was added, and the reaction mixture was heated to 90° C., and maintained at the temperature for 10 minutes. The reaction solution was passed through a C18 column to remove free ions, and then the C18 column was eluted with ethanol solution. Labeled $^{68}$Ga-TEFAPI-06 was obtained. The labeled $^{68}$Ga-TEFAPI-06 was diluted with normal saline, and 3.7 Mbq of the resulting solution was injected to each mouse. PET scanning imaging was performed at 0.5 h, 1.5 h, and 2.5 h, and PET image processing software was used for reconstruction. The obtained image is shown in FIG. 2, and it can be seen that the probe has obvious uptake at the tumor site.

Figure 3:
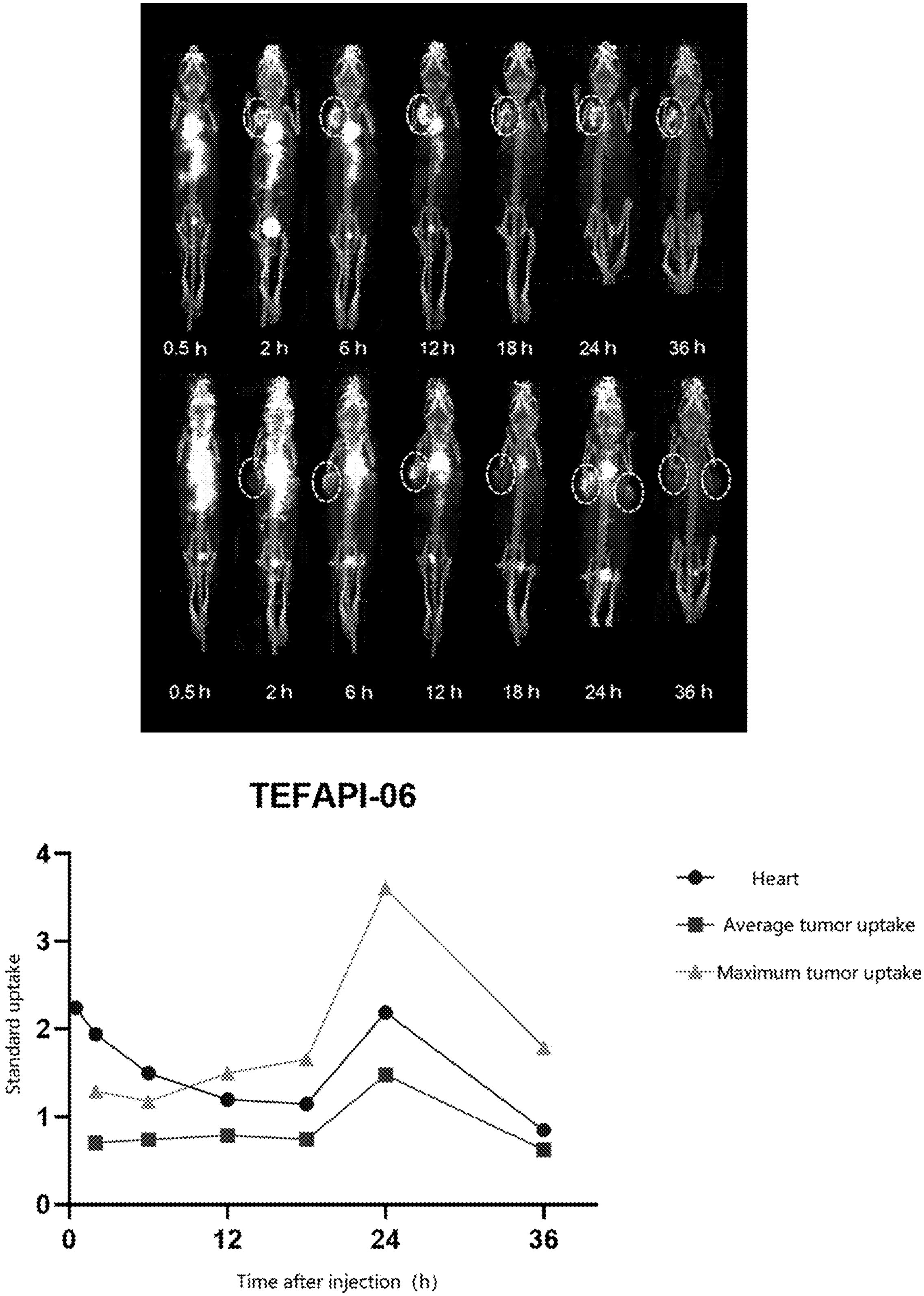
FIG. 3 shows results of long-duration PET imaging with $^{86}Y$-TEFAPI-06 in a PDX mouse model of pancreatic cancer.

IV. Long-Duration PET Imaging with $^{86}$Y-TEFAPI-06 in a PDX Mouse Model of Pancreatic Cancer Y-86 is a positron nuclide with half-life of 14.6 hours and can be radiolabeled with DOTA, and therefore, is very suitable for long-duration detection of the distribution of TEFAPI molecule in vivo. 1 mL of Y-86 hydrochloric acid was taken, 100 μL of 3M sodium hydroxide and 130 μL of 3M sodium acetate were added to adjust acidity, the final pH was 4.0, 50 μg of TEFAPI-06 precursor was added, and the reaction mixture was heated to 90° C., and maintained at the temperature for 10 minutes. The reaction solution was passed through a C18 column to remove free ions, and then the C18 column was eluted with ethanol solution. Labeled $^{86}$Y-TEFAPI-06 was obtained. The labeled $^{86}$Y-TEFAPI-06 was diluted with normal saline, and 7.4 Mbq of the resulting solution was injected to each mouse. PET scanning imaging was performed at 0.5, 2, 6, 12, 18, 24 and 36 h after injection, and PET image processing software was used for reconstruction. The obtained PET image is shown in FIG. 3, SUV values were marked at the tumor and heart of the mouse, and a curve was obtained based on the change of the SUV value with time. An SUV uptake curve of tumor uptake showed that the tumor uptake increased continuously in the first 24 hours, the blood circulation time was longer, and continuous clearance from the kidney was observed.

V. Competitive Inhibition Experiment of TEFAPI-06 in Mice with PDX Pancreatic Cancer In order to verify the specificity of TEFAPI-06 against a FAP target, the inventors performed PET imaging on the same batch of mice before and after inhibition in the competitive inhibition experiment. According to the Y-86 long-duration PET imaging, the uptake of the tumor reached a peak between 18 hours and 24 hours after drug injection. Therefore, $^{68}$Ga-FAPI-04 imaging was first performed on tumor-bearing mice to determine that the mice had tumor uptake. After 48 hours of standing to ensure metabolism of $^{68}$Ga-FAPI-04, two mice were injected with 300 μg of TEFAPI-06 molecules, and 18 hours after injection, PET molecular imaging of $^{68}$Ga-FAPI-04 was performed on the mice injected with TEFAPI-06 molecules. PET imaging results of $^{68}$Ga-FAPI-04 at 30 minutes after injection showed that there was significant uptake at the tumor when TEFAPI-06 was not injected, and there was no additional uptake at the tumor of mice after injection of TEFAPI-06 molecules.

Figure 4:
FIG. 4 shows results of a competitive inhibition experiment of TEFAPI-06 in mice with PDX pancreatic cancer.

As shown in FIG. 4, there was basically no additional uptake at the tumor of mice undergoing inhibition, but the same group of mice without inhibition showed higher uptake at the tumor. The results showed that the target site of TEFAPI-06 was FAP.

VI. Treatment of PDX Pancreatic Cancer in Mice with $^{177}$Lu-TEFAPI-06.

Figure 5:
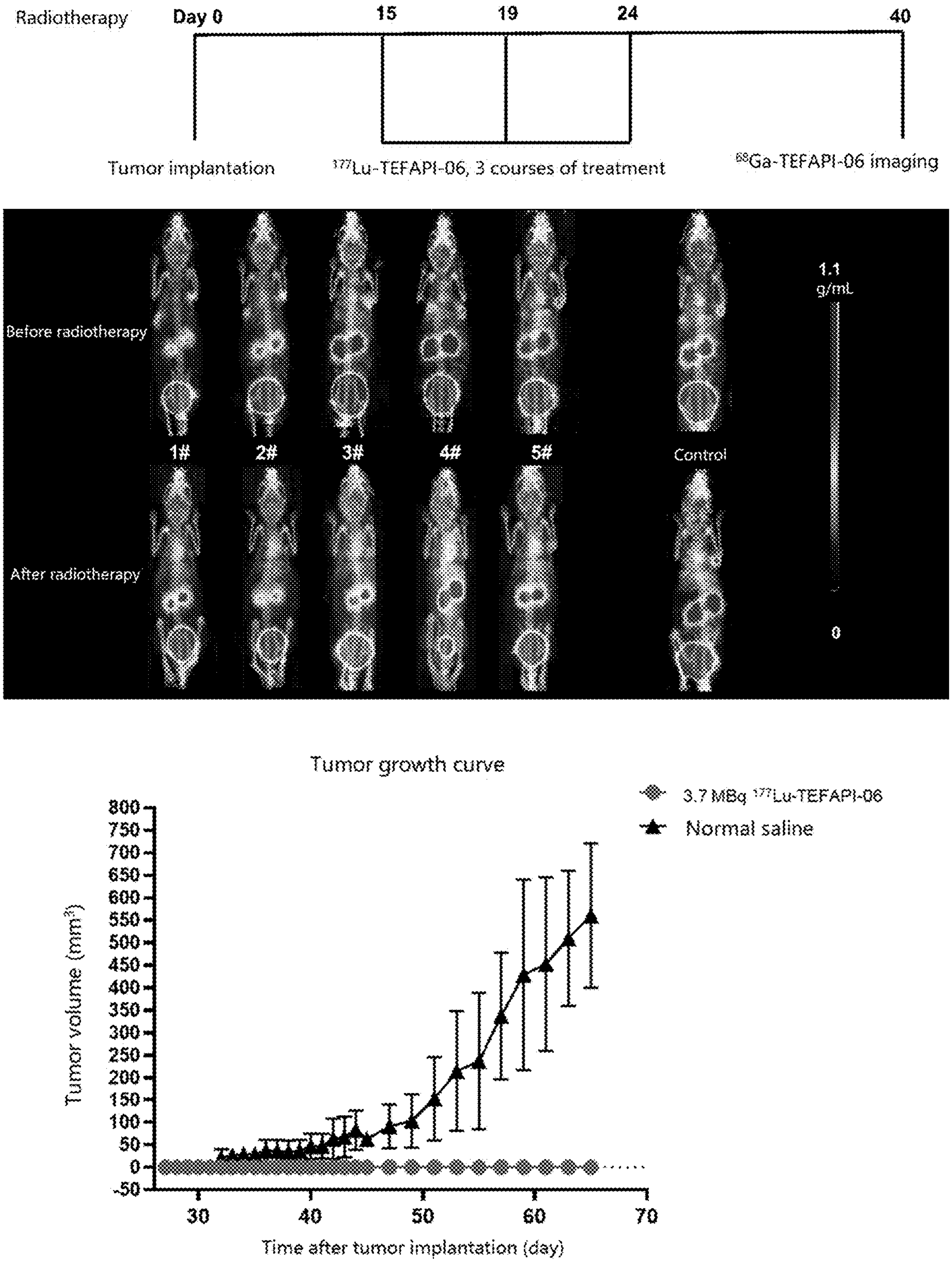
FIG. 5 shows results of treating PDX pancreatic cancer in mice with $^{177}Lu$-TEFAPI-06.

Based on the tumor targeting property of TEFAPI-06 and the metabolism rule of mice, and because its excellent tumor/normal tissue uptake ratio is greater than 10 after 18 hours, and kidney metabolism is basically cleared, mice with PDX pancreatic cancer were subjected to radioactive targeted therapy of Lu-177. There were 5 mice in each group. The treatment scheme is shown in the figure below. The treatment dose was 3.7 MBq. According to the tumor growth curve, the tumor in the treatment group was completely suppressed. In order to evaluate the therapeutic effect, the inventors performed physical examination via FAPI-04 imaging on mice before and after the treatment, and the results are shown in FIG. 5. It can be seen that after the treatment, the original tumor uptake in the mice had basically disappeared.

The above are only exemplary embodiments of the present invention, and are not intended to limit the protection scope of the present invention which is determined by the appended claims

What is claimed is:

1. A compound or a pharmaceutically acceptable salt, a stereoisomer or a solvate thereof, wherein the compound is

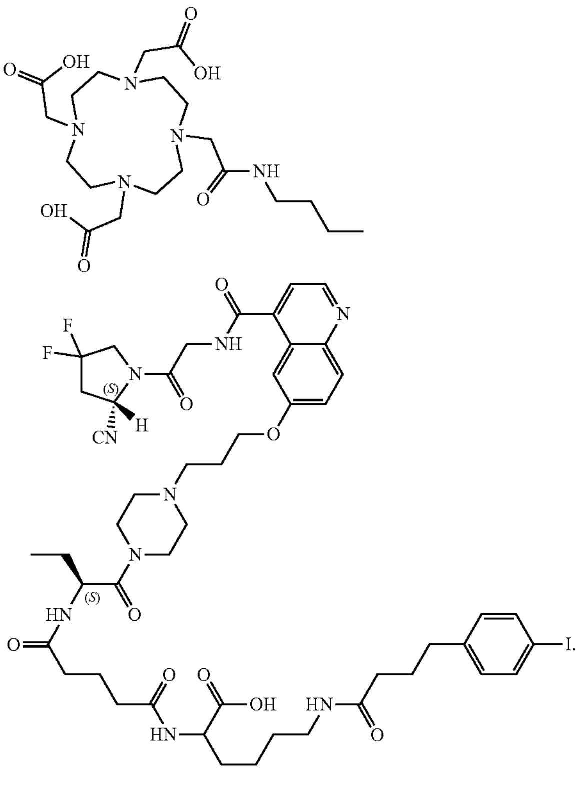

2. A chelate comprising the compound according to claim 1 and a radioactive nuclide.

3. The chelate according to claim 2, wherein the radioactive nuclide is selected from one or more of $^{18}$F, $^{51}$Cr, $^{67}$Ga, $^{68}$Ga, $^{111}$In, $^{99}$mTc, $^{186}$Re, $^{188}$Re, $^{139}$La, $^{140}$La, $^{175}$Yb, $^{153}Sm$, $^{166}Ho$, $^{86}Y$, $^{88}Y$, $^{90}Y$, $^{149}Pm$, $^{165}Dy$, $^{169}Er$, $^{177}Lu$, $^{47}Sc$, $^{142}Pr$, $^{159}Gd$, $^{212}Bi$, $^{213}Bi$, $^{72}As$, $^{72}Se$, $^{97}Ru$, $^{109}Pd$, $^{105}Rh$, $^{101m}Rh$, $^{119}Sb$, $^{128}Ba$, $^{123}I$, $^{124}I$, $^{131}I$, $^{197}Hg$, $^{211}At$, $^{151}Eu$, $^{153}Eu$, $^{169}Eu$, $^{201}Tl$, $^{203}Pb$, $^{212}Pb$, $^{64}Cu$, $^{67}Cu$, $^{188}Re$, $^{186}Re$, $^{198}Au$, $^{225}Ac$, $^{227}Th$ and $^{199}Ag$.

4. The chelate according to claim 3, wherein the radioactive nuclide is $^{68}Ga$, $^{86}Y$ or $^{177}Lu$.

5. A pharmaceutical composition comprising or consisting of:

at least one of the chelate according to claim 2, and optionally, a pharmaceutically acceptable excipient.

6. A method of diagnosing or treating a disease characterized by overexpression of fibroblast activation protein in a subject using the chelate according to claim 2.

7. The method according to claim 6, wherein the disease characterized by the overexpression of the fibroblast activation protein is selected from cancer, chronic inflammation, atherosclerosis, fibrosis, tissue remodeling and keloidosis.

8. A kit comprising the chelate according to claim 2, and an instruction for diagnosing or treating a disease.

9. A kit comprising the pharmaceutical composition according to claim 5, and an instruction for diagnosing or treating a disease.

10. A method of diagnosing or treating a disease characterized by overexpression of fibroblast activation protein in a subject using the pharmaceutical composition according to claim 5.

11. The method according to claim 10, wherein the disease characterized by the overexpression of the fibroblast activation protein is selected from cancer, chronic inflammation, atherosclerosis, fibrosis, tissue remodeling and keloidosis.

12. The method according to claim 7, wherein the cancer is selected from one or more of breast cancer, pancreatic cancer, small intestine cancer, colon cancer, rectal cancer, lung cancer, head and neck cancer, ovarian cancer, hepatocellular carcinoma, esophageal cancer, hypopharyngeal cancer, nasopharyngeal cancer, laryngeal cancer, myeloma cells, bladder cancer, cholangiocarcinoma, clear cell renal carcinoma, neuroendocrine tumor, carcinogenic osteomalacia, sarcoma, carcinoma of unknown primary, thymic carcinoma, glioma, neuroglioma, astrocytoma, cervical cancer and prostate cancer.

13. The method according to claim 11, wherein the cancer is selected from one or more of breast cancer, pancreatic cancer, small intestine cancer, colon cancer, rectal cancer, lung cancer, head and neck cancer, ovarian cancer, hepatocellular carcinoma, esophageal cancer, hypopharyngeal cancer, nasopharyngeal cancer, laryngeal cancer, myeloma cells, bladder cancer, cholangiocarcinoma, clear cell renal carcinoma, neuroendocrine tumor, carcinogenic osteomalacia, sarcoma, carcinoma of unknown primary, thymic carcinoma, glioma, neuroglioma, astrocytoma, cervical cancer and prostate cancer.

* * * * *